(12) United States Patent
Miller et al.

(10) Patent No.: US 6,372,446 B1
(45) Date of Patent: Apr. 16, 2002

(54) METHOD OF SELECTIVELY DETERMINING A FUNGAL BIOMASS

(75) Inventors: Morten Miller, Frederiksberg; Morten Reeslev, Copenhagen, both of (DK)

(73) Assignee: Mycometer ApS, Copenhagen (DK)

( * ) Notice: Subject to any disclaimer, the term of this patent is extended or adjusted under 35 U.S.C. 154(b) by 0 days.

(21) Appl. No.: 09/355,790

(22) PCT Filed: Jan. 30, 1998

(86) PCT No.: PCT/DK98/00041

§ 371 Date: Aug. 3, 1999

§ 102(e) Date: Aug. 3, 1999

(87) PCT Pub. No.: WO98/33934

PCT Pub. Date: Aug. 6, 1998

(30) Foreign Application Priority Data

Feb. 4, 1997 (DK) ............................................. 0129/97

(51) Int. Cl.$^7$ ............................................. G01N 33/53
(52) U.S. Cl. .......................... 435/7.31; 435/4; 435/7.1; 435/7.4; 435/7.72; 435/7.9; 435/34
(58) Field of Search ............................ 435/4, 7.1, 7.31, 435/7.4, 7.72, 7.9, 34

(56) References Cited

U.S. PATENT DOCUMENTS

| | | |
|---|---|---|
| 5,004,699 A | 4/1991 | Winters |
| 5,445,946 A | 8/1995 | Roth et al. |
| 5,474,926 A | 12/1995 | Harman et al. |
| 5,510,243 A | 4/1996 | Boyd et al. |

FOREIGN PATENT DOCUMENTS

| | | |
|---|---|---|
| DE | 19637909 | 3/1998 |
| EP | 0 054 001 A1 | 6/1982 |
| EP | 0 091 837 | 10/1983 |
| EP | 0 329 190 A2 | 8/1989 |
| EP | 0 347 771 A2 | 12/1989 |
| EP | 0 549 102 B1 | 6/1993 |
| FR | 81/08111 | 10/1982 |
| JP | 1296998 | 11/1989 |
| JP | 7 095 898 | 4/1995 |
| SU | 1557521 | 4/1990 |
| SU | 1 744 144 | 6/1992 |
| WO | 80/02458 | 11/1980 |
| WO | 86/05206 | 9/1986 |
| WO | 92/17786 | 10/1992 |
| WO | 95/23235 | 8/1995 |
| WO | 95/34678 | 12/1995 |
| WO | 96/31777 | 10/1996 |

OTHER PUBLICATIONS

M. Claeyssens, et al., Fungal cellulase systems: Comparison of the specificities of the cellobiohydrolases isolated from *Penicillium pinophilum* and *Trichoderma ressei*, Biochemical Journal, (1989) 261, 819–825.

D.W. Fink and W.R. Koehler, pH Effects on Fluroescence of Umbelliferone, Analytical Chemistry (1972), 42, 990–993.

Å. Frosteregård, Tunlid A. and E. Bååth, Phospholipid Fatty Acid Composition, Biomass and Activity of Microbial Communities from Two Soil Types Experimentally Exposed to Different Heavy Metals, Applied and Environmental Micribiology, Nov. 1993, 3605–3617.

W.D. Grant and A.W. West, Measurement of ergosterol, diaminopimelic acid and glucosamine in soil: evaluation as indicators of microbial biomass, Journal of Microbiological Methods 6, (1986), 47–53.

B.R. Kropp, Variable interactions between non–mycorrhizal and ectomycorrhizal strains of the basidiomycete Laccaria bicolor, Short Commuinications (1990), 412–415.

McCreath, K.J. and G.W. Gooday (1992), A rapid and sensitive microassay for determination of chitinolytic activity, Journal of Microbiological Methods 14, 229–237.

M. Reeslev, B.B. Jørgensen and O.B. Jørgen, Influence of $Zn^2+$on yeast–mycelium dimorphism and exopolysaccharide production by the fungus *Aureobasidium pullulans* grown in a defined medium in continuous culture, Journal of General Microbiology 139 (1993), 3065–3070.

H.T.S. Boschker and T.E. Capenberg, A Sensitive Method Using 4–Methylumbelliferyl–β–Cellobiose as a Substrate To Measure (1,4)–β–Glucanase Activity in Sediments, Applied and Environmental Microbiology, (1994) pp. 3592–3596.

Graham W. Gooday,et al., What are the roles of chitinases in the growing fungus? FEMS Microbiology Letters 100 (1992) 387–392.

Michael J. Kuranda and Phillips W. Robbins, Chitinase Is Required for Cell Separation during Growth of *Saccharomyces cerevisiae,* The Journal of Biological Chemistry, (1991) vol. 266, No. 29, Issue Oct. 15, pp. 19758–19767.

D.W. Zabriskie and A.E. Humphrey, Estimation of Fermentation Biomass Concentration by Measuring Culture Fluorescence, Applied and Environmental Microbiology, Feb. 1978, pp. 337–343.

(List continued on next page.)

*Primary Examiner*—Jennifer E. Graser
(74) *Attorney, Agent, or Firm*—Hunton & Williams

(57) ABSTRACT

A method for selectively determining a fungal biomass by detection of a fungal enzymatic activity that is present in substantially all fungal species, such as enzymes involved in chitin metabolism (chitinase, chitin synthase, chitosanase, N-acetyl-glucosaminidase and β-N-acetylhexosamidase). The invention can be used for detecting a fungal biomass in environmental samples, food products, plant material, building materials, industrial fungal cultures or sample from a human being or animal including blood samples. In particular, 4-methylumbelliferyl-N-acetyl-β-D-glucosaminide is used as substrate for β-N-acetylhexosamidase (EC 3.2.1.52). This enzyme activity correlates with the amount of fungal biomass present in a sample.

27 Claims, 12 Drawing Sheets

OTHER PUBLICATIONS

Mukoma F. Simpanya, Identification of *Candida albicans* and *C. tropicalis* with an unbellifery–labelled galactosaminide, J.Med. Microbiol., vol. 43 (1995), 230–233.

Patricia Rousselle, et al., Rapid Identification of *Candida albicans* by using Albicans ID and Fluoroplate Agar Plates, Journal of Clinical Microbiology, vol. 32, No. 12, Dec. 1994, pp. 3034–3036.

Jack L. Perry, et al., Rapid, Colorimetric Identification of *Candida albicans,* Journal of Clinical Microbiology, vol. 28, No. 3, Mar. 1990, pp. 614–615.

Maurice T. Dalton, et al., Rapid Identification of *Candida albicans* Using 4–Methylumbelliferyl N–acetyl–β–galactosaminide, Diagn Microbiol Infect Dis, 1989, 12:521–523.

Catherine M. Smitka and Susan G. Jackson, Rapid Fluorogenic Assay for Differentiation of the *Candida parapsilosis* Group from Other *Candida* spp., Journal of Clinical Microbiology, vol. 27, No. 1, Jan. 1989, pp. 203–206.

Jack J. Perry and Glendon R. Miller, Umbelliferyl–Labeled Galactosaminide as an Aid in Identification of *Candida albicans,* Journal of Clinical Microbiology, vol. 25, No. 12, Dec. 1987, pp. 2424–2425.

Morten Miller et al., The Use of Flurogenic Substrates To Measure Fungal Presence and Activity in Soil, Applied and Environmental Microbiology, Feb. 1998, pp. 613–617.

R. Rodriquez–Kabana, G. Godoy, G. Morgan–Jones and R.A. Shelby, The determination of soil chitinase activity; Conditions for assay and ecological studies, Plant and Soil 75, 95–106 (1983).

Gertrud Wiese, et al., An Improved Procedure for the Quantative Estimation of the Rust Fungus in Infected Plant Tissue, Z. Naturforsch, 41(c) 1127–1130, 1986, pp. 1127–1130.

Frostegård, A. and Bååth, E. (1996) The Use of Phospholipid Fatty Acid Analysis to Estimate Bacterial and Fungal Biomass in Soil; Biol. Fertil. Soils 22,59–65.

METHOD OF SELECTIVELY DETERMINING A FUNGAL BIOMASS

FIELD OF INVENTION

The present invention relates to the field of determining fungal biomass in a variety of samples including environmental samples, food products, plant materials, building construction materials, human and animal body samples and industrial fungal cultures.

TECHNICAL BACKGROUND AND PRIOR ART

Fungal species are used in the fermentation of foods and for the production of desired gene products like enzymes and antibiotics. Fungi may also cause spoilage of foods and agricultural products, cause rot in building materials, and may be pathogenic to mammals including humans.

Currently used methods for detecting fungal biomass include extracting fungus specific cell components such as ergosterol (Grant and West, 1986) and phospholipid fatty acids (PLFA) (Frostegård et al., 1993), selectively staining cellular organelles (Kropp, 1990; U.S. Pat. No. 5,445,946), fluorescently detecting fungal metabolites present in cellular extracts (SU 1,744,114; JP 7,095,898), and immunological detection of structural components of the fungal cell wall (U.S. Pat. No. 5,004,699).

However, all of these methods involve several drawbacks, in particular due to complicated sample preparations including disruption of cells and hyphae and isolation of cell components. In addition, the methods generally involve extended assay periods and besides, they are time consuming, laborious and require specialised technical skills.

There is therefore a need for an improved, simple and rapid method of selectively determining fungal biomass which can be performed without the above drawbacks.

It has now been found that a reproducible correlation exists between certain enzymatic activities which is present in substantially all fungal species, and the amount of fungal biomass and/or the amount of fungal cell components. This discovery has led to the development of a novel method of determining fungal biomass that fulfills the above need for an improved method.

SUMMARY OF THE INVENTION

Accordingly, the present invention pertains in one aspect to a method of selectively detecting a fungal biomass in a sample, comprising detecting the amount, presence or activity of at least one enzyme that is present in substantially all fungal species, the amount or activity of which enzyme is correlated with the amount of fungal biomass present in the sample, the detection being made under conditions where enzymes of non-fungal origin, if present, cannot be detected. In particular, there is provided a method comprising the steps of (i) contacting a sample with a substrate molecule comprising a detectable moiety releasable from said substrate molecule in the presence of a selectively detectable fungal enzymatic activity, and (ii) detecting the released moiety.

In a further aspect, the invention pertains to a product comprising (i) an agent that reacts with an enzyme that is present in substantially all fungal species and the amount or activity of which enzyme is correlated with the amount of fungal biomass present in a sample, the reaction between the enzyme and the agent resulting in a detectable signal and (ii) means for detecting said signal, as a combined system for the detection of a fungal biomass present in the sample.

DETAILED DISCLOSURE OF THE INVENTION

The invention provides, as it mentioned above, a method of selectively detecting a fungal biomass in a sample, comprising detecting the amount, presence or activity of at least one enzyme being present in substantially all fungal species and the amount or activity of which is correlated with the amount of fungal biomass present in the sample.

As used herein, the expression "selectively detecting" indicates that, when a sample is tested in accordance with the invention, the test conditions are selected so as to exclude any detection of non-fungal enzymes or enzymatic activities which could otherwise interfere with a selective assay for fungal enzymes.

In the present context, the expression "fungal biomass" refers to any cellular components of fungal species as they are defined in Henderson's Dictionary of Biological Terms, 10th edition, Longman Scientific & Technical, 1990. Thus, as used herein fungal biomass includes single cells, mycelia, thalli, hyphae and spores of the fungal species mentioned in the above reference book. Fungal species as defined herein include species belonging to the subdivisions Zygomycotina, Ascomycotina, Basidiomycotina and Deuteromycotina.

In one embodiment, the method of the invention is based on the detection in a sample to be tested of the activity of at least one fungal enzyme by contacting the sample with a substrate molecule comprising a detectable moiety releasable from said substrate molecule in the presence of the fungal enzyme followed by detecting the released moiety.

Thus, an assay for detecting a fungal enzymatic activity can be based upon specific cleavage of a substrate molecule into one or more readily detectable moieties. Fluorogenic moieties can be detected with a high sensitivity and the use of substrate molecules comprising fluorescently detectable moieties in conventional assays of enzymatic activities is well characterised and can be used in accordance with the invention. As an example, the high sensitivity of detection of fluorogenic moieties has facilitated the development of assays for the detection of e.g. chitinase produced by bacterial species (McCreath and Gooday, 1992) and β-glucanase activities in fungal species, including yeast (Claeyssens et al., 1989)

Thus, the present method can include the detection of an enzymatic activity that is associated with the metabolism of cell structural components. As used in this context, the expression "structural components" includes naturally occurring substances which confer rigidity and mechanical strength to fungal cell walls including septae such as e.g. chitin, chitosan, cellulose, glycogen, glucan, polygalactosamine and polypeptides.

Fungal enzymatic activities which can be used in the present method include those naturally produced in a fungal biomass to be detected. Alternatively, a detectable fungal enzymatic activity in a given fungal biomass can be expressed from a gene inserted by genetic recombination.

In accordance with the invention, detectable enzymatic activities are preferably activities that are expressed constitutively, expressed in all growth phases of the fungal biomass and/or expressed independently of the physiological state of the fungal biomass. The enzymatic activities can be cell associated and/or extracellular.

In other embodiments, the method is based on a detectable enzymatic activity which is expressed in both the presence and absence of biologically cleavable polymers present in a fungal cell wall, such as e.g. chitin, glucans and polypeptides. In yet another embodiment, the detectable enzymatic activity is expressed in both the presence and absence of biologically cleavable polymers such as polysaccharides e.g. including cellulose, hemicellulose, amylose, amylopectin, mannan, xanthan, xylan, arabinan and galactan or is a fungal enzymatic activity that degrades any of such polysaccharides or polypeptides. A presently preferred embodiment of the method according to the invention is based on the detection in a sample of an enzymatic activity selected from an enzyme hydrolysing β-(1-4) bonds between N-acetyl-hexosaminide groups and an enzyme synthesising such bonds. In this connection, β-(1-4) bond hydrolysing enzymes include any fungal enzymatic activity that hydrolyses such bonds in polymers and glycosylated proteins containing N-acetylglucosaminide groups, such as the polysaccharides chitin and/or chitosan which are present in substantially all fungal species.

Accordingly, the present method can be based upon detection of a fungal enzymatic activity associated with chitin metabolism, in particular a chitinase (E.C. 3.2.1.14), a β-N-acetylhexosaminidase (E.C. 3.2.1.52) and/or a chitin synthase (E.C. 2.4.1.16). Alternatively, the method is based on an enzymatic activity that is associated with the metabolism of chitosan, i.e. an at least partially deacetylated chitin. An example of such an enzyme activity is chitosanase (E.C. 3.2.1.132) (The above E.C. numbers refer to Enzyme Data Bank, Release 21.0/October 1996).

Besides being based on detection of the activity of a fungal biomass associated enzymatic activity, the present method encompasses any other assay procedure permitting the detection of a fungal enzyme, the amount of which is correlated with the fungal biomass. Such procedures include as examples detecting the amount of the fungal enzyme immunologically and the detection of DNA and/or RNA sequences coding for the enzymatic activity of interest. Such procedures can be based on methods which are well-known in the art and include e.g. the use of antibodies, optionally labelled with detectable moieties and the use of oligonucleotide probes that hybridizes selectively to the DNA or RNA sequences.

It is a significant aspect of the present invention that a wide variety of fungal species, when tested for their ability to enzymatically cleave substrates labelled with fluorogenic moieties, produce an enzymatic activity releasing fluorescently detectable moieties, the amount of which is correlated with the amount of ergosterol and fungus related phospholipid fatty acids (PLFA), the presence of which are currently used in the determination of a fungal biomass.

Surprisingly, the amount of the released fluorescently detectable moieties is directly correlated with the biomass of the assayed fungal species producing the above enzymatic activity. This correlation is indicative of a constitutive expression of the substrate cleaving enzymatic activity.

In another preferred embodiment the method comprises a further step of correlating the activity or the amount of fungal enzyme with a fungal biomass parameter of the fungal biomass such as e.g. the amount of fungal biomass present in the sample, as determined by directly measuring the weight of the fungal biomass. The fungal biomass parameter can also be a metabolite, an additional enzymatic activity or an indicator of the physiological state of said fungal biomass. In this context, suitable fungal metabolites include fatty acids, polysaccharides and parts hereof, polyketides, steroids, shikimic acids, alkaloids, a pigment naturally produced by a fungal species such as e.g. astaxanthin, carotenoids, riboflavins, terpenoids and derivatives hereof, antibiotics such as e.g. penicillins.

In a particular embodiment of the method according to the invention, a detectable moiety released from a substrate for the fungal enzyme is correlated with the amount of fungal biomass present in the sample as determined directly by measuring the weight of the fungal biomass. Preferably the weight is the dry weight of the fungal biomass. Having established such a correlation in the form of e.g. a standard curve, the method can be used to establish further suitable standard curves e.g. illustrating, under appropriate experimental and/or industrially relevant conditions, the relationship between the amount of released moiety and the amount of the fungal biomass. Standard curves may be produced for a number of experimental and/or industrially relevant conditions so as to provide a set of physiological parameters associated with the physiological state of a fungal species under a variety of conditions. Such parameters include growth rate, growth phase, temperature, pH, oxygen content, growth medium composition including the presence/absence of preferably metabolisable nutrients, osmotic strength, and the presence or absence of essential cell constituents or precursors herefor.

The indicator of the physiological state of said fungal biomass shall also be understood to include the presence or absence of certain metabolites or polypeptides produced i) in certain growth phases, ii) in response to changing environmental conditions, or iii) in response to the presence or absence of cellular or chemical components.

The correlation between the released detectable moiety and an indicator of the physiological state of the fungal biomass can also be applied to establish a reliable method for assessing "physiological fitness and adaptability" of a fungal biomass. This is particularly important in the detection of a fungal biomass which is genetically engineered, selected or otherwise improved for a particular purpose, typically an increased production of a metabolite, an antibiotic or a desired gene product. Thus, the production in large amounts of homologous and/or heterologous polypeptides may lead to misfolding of the produced polypeptide and/or overloading of the cellular transport or secretion apparatus. These undesirable phenomena are likely to induce a stress response which, when present in a "semi-permanent state", is likely to reduce the production yield. In accordance with the present method, a detectable moiety that is released by the fungal enzymatic activity can be detected by any spectroscopic method. Thus, suitable spectroscopic methods include methods for determining a selective absorption of electromagnetic radiation by substrate molecules and moieties released herefrom such as fluorometry, wherein the fluorescence emitted by the released moiety is determined. A selective detection of a released and fluorescently detectable moiety can also be achieved by using a filter absorbing light of all but desired, predetermined wavelengths, which pass through the filter prior to being detected.

When it is desired to detect more than one substrate moiety, the different moieties should emit fluorescence which is detected at different wavelengths and/or by using suitable filters as described above.

Alternative methods of detecting selective absorption of electromagnetic radiation include ultraviolet spectroscopy, infrared spectroscopy, nuclear magnetic resonance (NMR) spectroscopy, including pulsed Fourier transform NMR, mass spectrometry, X-ray diffraction, microwave absorption, electron spin resonance, optical rotatory dispersion and circular dichroism.

Ultraviolet spectroscopy is used to detect conjugated systems, because the promotion of electrons from the ground state to the excited state of such systems gives rise to absorption in this region of the spectrum. Infrared spectroscopy is used to detect and identify the vibrations of molecules and in particular the characteristic vibrations of the double and triple bonds present in many functional groups.

Nuclear magnetic resonance spectroscopy uses a longer wavelength of the electromagnetic spectrum to detect changes in the alignment of nuclear magnets in strong magnetic fields. The precise frequency of absorption is a very sensitive measure of the magnetic, and hence the chemical, environment of such nuclei. Moreover, the number and disposition of neighbouring magnetic nuclei influence the appearance of that absorption in a well-defined way. The result is a considerable information about the arrangement of functional groups and hydrocarbon residues in e.g. a moiety part of or released from the substrate molecule.

Mass spectrometry measures the mass-to-charge ratio of substrate moieties which have been charged by electron bombardment. Structural information comes from the moderately predictable fragmentation of substrate molecules, including a correlation of charged moieties with likely structures. X-ray diffraction can be used to identify centres of high electron density, such as e.g. atoms. Microwave absorption is used to measure molecular rotations of substrate moieties.

Electron spin resonance detects unpaired electrons and can be used to measure the distribution of electron densities in substrate moieties such as e.g. released radicals. Optical rotatory dispersion and circular dichroism use visible and ultraviolet light for determining the correlation of changes in rotatory energy of substrate moieties with changes of polarized light; such measurements can often be related to the absolute configuration of molecules.

Thus, it will be understood that moieties are "selectively" detectable by application of results obtainable from one or more of the above-mentioned methods, such as e.g. UV maxima, IR frequencies, NMR chemical shifts and coupling constants, and common mass fragments found in mass spectra.

The method of the invention is suitable for the detection of fungal biomass including species belonging to Zygomycotina, Ascomycotina, Basidiomycotina and Deuteromycotina, or a mixture hereof. In one embodiment the invention pertains to the detection of fungal biomass comprising viable propagules in the form of mycelia, conidia, spores and single cells, such as yeast. In another embodiment of the invention, the fungal biomass in the assayed sample comprises viable fungal biomass and/or non-viable fungal biomass.

The method can be used to detect fungal biomass in small amounts such as an amount which is at the most 1 $\mu$g, preferably at the most 0.1 $\mu$g, more preferably at the most 0.01 $\mu$g and most preferably at the most 0.001 $\mu$g is detectable.

In one embodiment, the method according to the present invention comprises the further step of pre-incubating the sample in a suitable medium supporting the growth of fungal biomass, prior to the actual assaying for the presence hereof. The objective of the pre-incubation is to allow any fungal biomass to propagate and thus contribute to an increased sensitivity of the assaying procedure described herein below. The pre-incubation can include adding a compound inhibiting non-fungal biological activity to a suitable growth medium. Compounds that are useful for inhibiting non-fungal biological activities include antibiotics, such as e.g. chloramphenicol and/or streptomycin, bacteriocins and chemicals having selective growth inhibiting effects on bacteria, such as e.g. sulphites or metal ions. The length of the pre-incubation period depends on the amount of fungal biomass and the amount of non-fungal biomass present in the sample.

In accordance with the present method, a sample can be pre-incubated several times under conditions selectively suppressing pressing growth of fungal biomass or non-fungal biomass. Such pre-incubations can precede a series of assaying procedures wherein i) the total biomass is determined quantitatively (i.e. no suppression of growth), ii) fungal biomass is determined quantitatively (i.e. suppression of growth of non-fungal biomass), and iii) non-fungal biomass is determined quantitatively (i.e. suppression of growth of fungal biomass).

The present method may include the addition of an inducer substance capable of inducing or enhancing the detectable fungal enzymatic activity. The inducer can be added i) during the pre-incubation period as mentioned above, ii) immediately prior to the assay procedure or iii) at suitable time intervals during the assay procedure. When it is preferred to determine the presence of non-fungal biomass, the addition of an inducer substance capable of inducing or enhancing the non-fungal enzymatic activity can be added.

Useful inducers include monomers and/or oligomers, such as e.g. dimers and trimers, of substances making up polysaccharides such as e.g. cellulose, hemicellulose, amylose, amylopectin, chitin, mannan, xanthan, xylan, arabinan and galactan. Particularly useful inducers are glucosamines, such as e.g. N-acetyl-glucosamine and amino-substituted derivatives hereof.

In yet another embodiment, the method according to the invention comprises, following the assay procedure, a further step of incubating the sample in a suitable selective medium permitting growth of only i) fungal biomass or ii) non-fungal biomass. Growth of non-fungal biomass, such as e.g. bacteria, may thus lead to determining bacterial species comprised in the sample by using state of the art techniques. Similarly, the fungal biomass comprised in the sample may be further differentiated or identified by growth on selective media supplemented with e.g. a particular carbon source, which supports growth and/or the development of phenotype traits of one or more fungal species e.g. belonging to Zygomycotina, Ascomycotina, Basidiomycotina or Deuteromycotina.

In the detection of enzymatic activity in accordance with the invention, useful substrate molecules comprising fluorescently and/or chromogenically detectable moieties are particularly preferred such as substrate molecules including a fluorogenic and/or chromogenic moiety such as a 4-methylumbelliferone moiety or derivatives hereof, e.g. 4-methylumbelliferyl-N-acetyl-$\beta$-D-glucosaminide (4-MU-GlcNAc). It has been found that substantially all fungal species are capable of constitutively cleaving this substrate whereas none of a range of bacterial species tested had this capability.

Alternative substrate molecules include 5-bromo-6-chloro-3-indolyl-2-acetamido-2-deoxy-$\beta$-D-glucopyranoside, 5-bromo-4-chloro-3-indolyl-N-acetyl-$\beta$-D-glucosaminide, indolyl-2-acetamido-2-deoxy-$\beta$-D-glucopyranoside, 4-nitrophenyl-N-acetyl-$\beta$-D-glucosaminide, $\beta$-trifluoromethylumbelliferyl-N-acetyl-$\beta$-D-glucosaminide, N-methylum-indolyl-N-acetyl-$\beta$-D-glucosaminide, 5-iodo-3-indolyl-N-acetyl-$\beta$-D- glucosaminide, 4-methylumbelliferyl-β-D-N,N',N"-triacetylchitotriose, 4-methylumbelliferyl-β-D-N,N'-diacetylchitobioside, 4-methylumbelliferyl-7-(6-sulfo-2-acetamido-2-deoxy)-β-D-glucosaminide, 4-methylumbelliferyl-7-(6-sulfo-2-acetamido-2-deoxy-β-D-glucopyronoside), 4-methylumbelliferyl-N-acetyl-α-D-glucosaminide, 4-methylumbelliferyl-N-acetylgalactosaminide, resorufin-N-acetyl-β-D-glucosaminide, 4-methylumbelliferyl-N-acetyl-α-D-glucosaminide and DDAO (9H-(1,3-dichloro-9,9-dimethylacridin-2-one-7-yl)N-acetyl-β-D-glucosaminide) and all N-actyl-β-D-glucosaminide oligomer derivatives of DDAO.

In preferred embodiments of the invention, the released fluorometrically and/or chromogenically detectable moiety is detectable in an amount of at the most 100 picomoles, preferably at the most 50 picomoles, more preferably at the most 20 picomoles, even more preferably at the most 10 picomoles and most preferably, the released moiety is detectable in an amount of at the most 1 picomole.

Although preferred embodiments of the invention pertain to a fluorometric and/or chromogenic detection of the released moiety, the method includes an embodiment wherein the released moiety is visibly detectable e.g. by luminescence without any further quantification or data processing.

The invention also provides a method comprising the further step of using at least one additional substrate molecule comprising a releasable moiety which is detectable. This moiety may be released either by a fungal enzymatic activity, a general microbial enzymatic activity or a non-fungal enzymatic activity.

The detectable moiety comprised in the additional substrate molecule may thus serve to differentiate between, or further facilitate identification of, i) one or more fungal species comprised in the sample, ii) microbial biomass comprised in the sample and iii) non-fungal biomass comprised in the sample.

Use of the method according to this particular embodiment would thus facilitate a selective detection in the sample of interest of microbial biomass, fungal biomass and non-fungal biomass, respectively. This is particularly relevant when the sample to be assayed is obtained from an environment also permitting growth of e.g. non-fungal biomass.

Although primarily providing the means of determining a fungal biomass, the method may also in particular embodiments be used in the determination of a particular fungal species, a particular microbial biomass or a non-fungal biomass. Thus, it is well known that chitin is a major polysaccharide of the cell wall of fungi. Chitin cleaving enzymes facilitating incorporation of the monomeric elements of chitin, N-acetyl-glucosamine, into the fungal cell wall may thus be considered candidates for selectively detectable fungal enzymatic activities.

By analogy, the present invention provides, in one contemplatable embodiment, a method of determining e.g. a particular fungal species, a particular microbial biomass or non-fungal biomass based on the presence of selectively detectable enzymatic activities either cleaving or synthesising polysaccharides.

As one example of such a contemplatable embodiment, the fungal species *Penicillium charlesii* produces a furanose linked polysaccharide comprising galactan, when grown on glucose whereas, in the absence of glucose or during starvation, this polysaccharide is believed to be cleaved by a galactan cleaving enzymatic activity present in *Penicillium charlesii*. Detection of this enzymatic activity can be used to selectively detect *Penicillium charlesii*.

In terms of determining bacterial biomass, reference can be made to dextran synthesising strains of Leuconostoc growing on sucrose. Enzymatic activities capable of synthesising dextran may thus form the basis of determining Leuconostoc biomass. In yet another example, the xanthan synthesising activities of *Xanthomonas campestris* could form the basis of a method of determining this bacterial species.

In a further example, the bacterial polysaccharide curdlan is produced by *Alcaligenes faecalis* and the detection of enzymatic activities involved in this production may be used to selectively determine *Alcaligenes faecalis* biomass.

In accordance with the invention, the time period of contacting the sample with the substrate molecule is at the most 24 hours, preferably at the most 6 hours, such as at the most 3 hours, more preferably at the most 30 minutes, even more preferably at the most 10 minutes such as at the most 1 minute and most preferably, the time of contacting the sample with the substrate molecule is at the most 30 seconds. The samples can be assayed in micro-titre plates.

The method of the invention may include collection of samples and/or detection of the released moiety at suitable time points over a suitable time interval. There is also provided a method according to the invention wherein the released moiety is detected continuously e.g. by on-line analysis. The substrate molecule may initially be added once and remain present while samples are collected over the desired time period. Alternatively, the substrate molecule is added in an appropriate amount at each point in time immediately prior to detecting the released moiety. When quantitative detection of the released moiety is desired, the substrate molecule must be present at a concentration representing "saturation". This can also be achieved by using subsaturation concentrations if only 10–20% of the substrate molecules are cleaved, preferably at a constant "turnover" rate, so as to release the detectable moiety at a constant rate over a suitable time interval.

The wide range of applications based on the present method is illustrated by the fact that the sample may be contacted with a substrate molecule either in a liquid or a solid medium. Thus, both fungal and bacterial species can be screened for enzymatic activity by using a suitable solid medium, such as e.g. soil extract agar (SEA) medium, supplemented with 4-MU-GlcNAc. The screening medium may also be supplemented with, substances having potential inducing effects as it is described in the following examples.

Contacting a sample with the substrate molecule may also lead to "in situ detection" of a fungal biomass. As used herein, "in situ detection" designates determination of the fungal biomass in its place of growth such as e.g. a natural habitat. There is also provided a method for determining fungal biomass present beneath the outer surfaces of the sample.

In particularly preferred embodiments of the invention, the sample is an environmental sample collected from soil, water or air. The sample can also be obtained or derived from a building element or be a sample of wood. In one particular embodiment, there is provided a method of detecting Tuberaceae and/or Cantharellus biomass in a sample collected from soil. State of the art methods currently available for determining Tuberaceae biomass requires, besides being time consuming and elaborative, the use of experimental animals, such as e.g. pigs.

In accordance with the invention, fermented products for human or animal consumption, a field crop or part hereof, a plant or part hereof, a vegetable and a fruit can be assayed for the presence of fungal biomass. Assaying grains, seeds or nuts for the presence of fungal biomass is a particularly useful application.

In other applications, a sample of a field crop, a plant, a vegetable or a fruit is assayed and the results can be evaluated in the context of monitoring and controlling the distribution and efficacy of fungicides. Harvested products are assayed, in particular during storage, to evaluate the level of fungal contamination. The harvested products can be assayed by directly contacting a sample hereof with the substrate as described above or by first preparing a suitable extract from the harvested product to be assayed.

The method is suitable for assaying a food product e.g. a heat processed food product, a food component, a feed product and a feed component. Assaying a spice, tea, cocoa or coffee is also a useful application.

Use of the provided methods for the quantitative detection of fungal biomass generates reliable results in a sensitive manner. The obtained results can be used in evaluating compliance with general health and/or safety guidelines. In some cases, such results may be generated on the basis of non-quantitative detection of fungal biomass.

As an example of the use of the method in evaluating compliance with general health and/or safety guidelines, the ecologically and/or toxicologically effects of e.g. chemicals including organic compounds having putatively undesirable effects on an environment can be assessed. Such chemicals are added to selective samples of e.g. soil comprising a fungal biomass and the effect of the chemical on the growth of the fungal species is determined. In one particularly interesting embodiment, the diffusion of fungicides into a sample of soil supplemented with a fungal biomass is evaluated in terms of monitoring the survival of the fungal biomass. This survival may be correlated to traditional fungus indicators, such as e.g. ergosterol and PLFA.

In a particular application of the method, the sample comprises a fungal biomass used in the production of a desired product in the form of a peptide, such as a polypeptide, an enzyme, an epitope, a hormone, an anti-viral protein, an anti-tumour protein and a growth factor. The fungal biomass may also be used in the production of a desired metabolite or a cellular component. The above fungal biomass may comprise at least one recombinant fungal species or a species comprising a gene and/or expression signals not naturally associated with said fungal species. The term "recombinant" refers to any form of genetic engineering used to produce the recombinant species. The fungal biomass may also be one wherein the production of a polypeptide, a metabolite and/or a cellular component has been reduced or eliminated, said reduction and/or elimination being achieved by traditional screening techniques or by techniques involving recombinant genetics and/or genetic engineering.

In a complatable aspect of the invention, means for detecting the released moiety by e.g. a fluorometer is provided. Accordingly, the invention also pertains to an apparatus for fluorometrical and/or chromogenical detection of released and detectable moieties generated in the method described above. The apparatus is suitably a portable apparatus which can be used for "platform" or field tests.

In yet another contemplatable aspect of the invention, there is provided a method of determining a microbial biomass by detection of a detectable enzymatic activity present in said biomass. In particular, there is provided a putative method comprising the steps of (i) contacting a sample with a substrate molecule comprising a detectable moiety releasable from said substrate molecule in the presence of a selectively detectable microbial enzymatic activity, and (ii) detecting the released moiety.

A further interesting application of the present method is, the detection of fungal infections in humans and animals. Thus, it was found that the method permitted the detection of fungally derived β-N-acetylhexosaminindase present in human plasma samples. However, it was also discovered that human plasma samples have an inherent hexosaminidase activity, which could be removed from the plasma e.g. by precipitation with ammonium sulphate. Such a pretreatment did not affect the detection of the fungally derived β-N-acetylhexosaminidase also present in the plasma. It is envisaged that the present method can be used generally for detection of fungi or fungally derived enzymatic activity in body samples from humans and animals.

The invention pertains, as it is mentioned above, to a product comprising (i) an agent that reacts with an enzyme that is present in substantially all fungal species and the amount or activity of which enzyme is correlated with the amount of fungal biomass present in a sample, the reaction between the enzyme and the agent resulting in a detectable signal and (ii) means for detecting said signal, as a combined system for the detection of a fungal biomass present in the sample. Thus, the agent of such a product can be selected from a substrate molecule comprising a detectable moiety releasable from said substrate molecule in the presence of the fungal enzyme, an immunologically active compound including a polyclonal or monoclonal antibody capable of binding to the fungal enzyme, and a nucleotide sequence that is capable of hybridizing to a DNA or RNA sequence coding for the fungal enzyme of interest.

Suitable means for detecting the signal include a spectrometer of any of the above types.

The invention is further illustrated in the below examples and the drawing wherein FIGS. 1 and 2 illustrates the highly significant, positive correlation between the β-N-acetylhexosamidase activity and estimates of the amount of the currently used fungal indicator PLFA, in selected soil samples. The β-N-acetylhexosamidase activity is measured as the release of 4-methylumbelliferone (4-MU) from 4-methylumbelliferyl-N-acetyl-β-D-glucosaminide, measured in nanomoles of 4-MU released per hour per g soil (dry weight);

Figure 7:
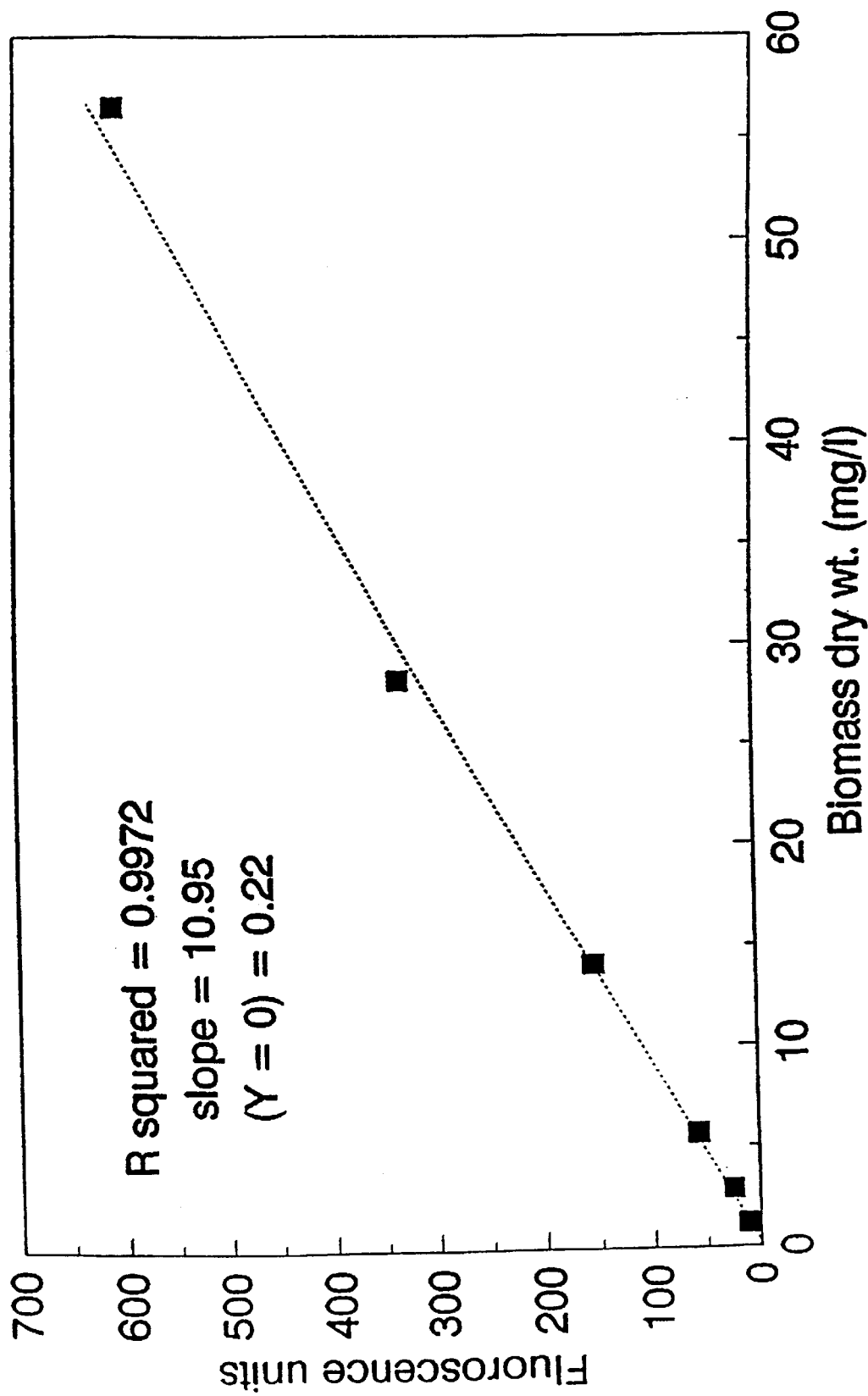
Figure 8:
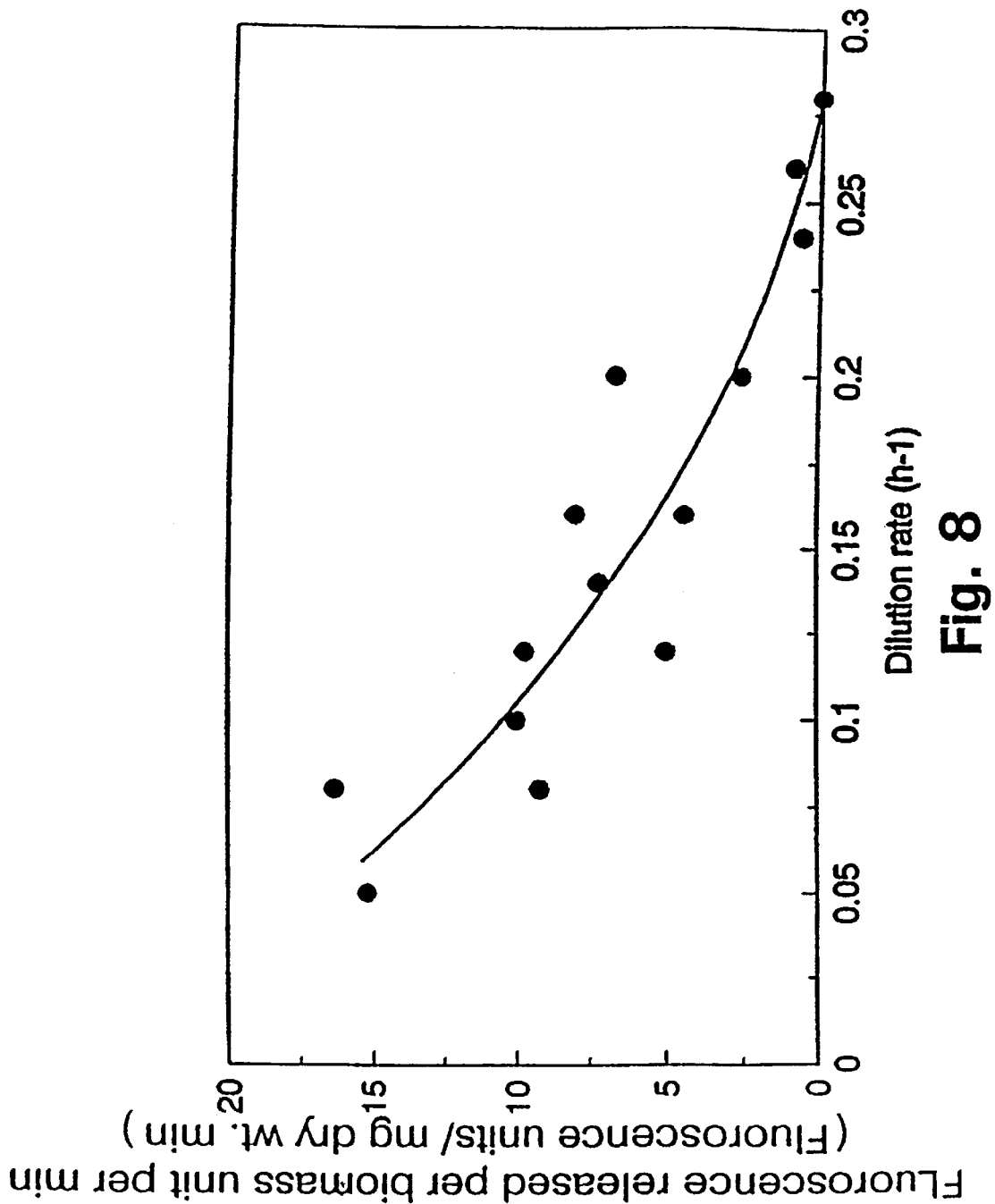
Figure 9:
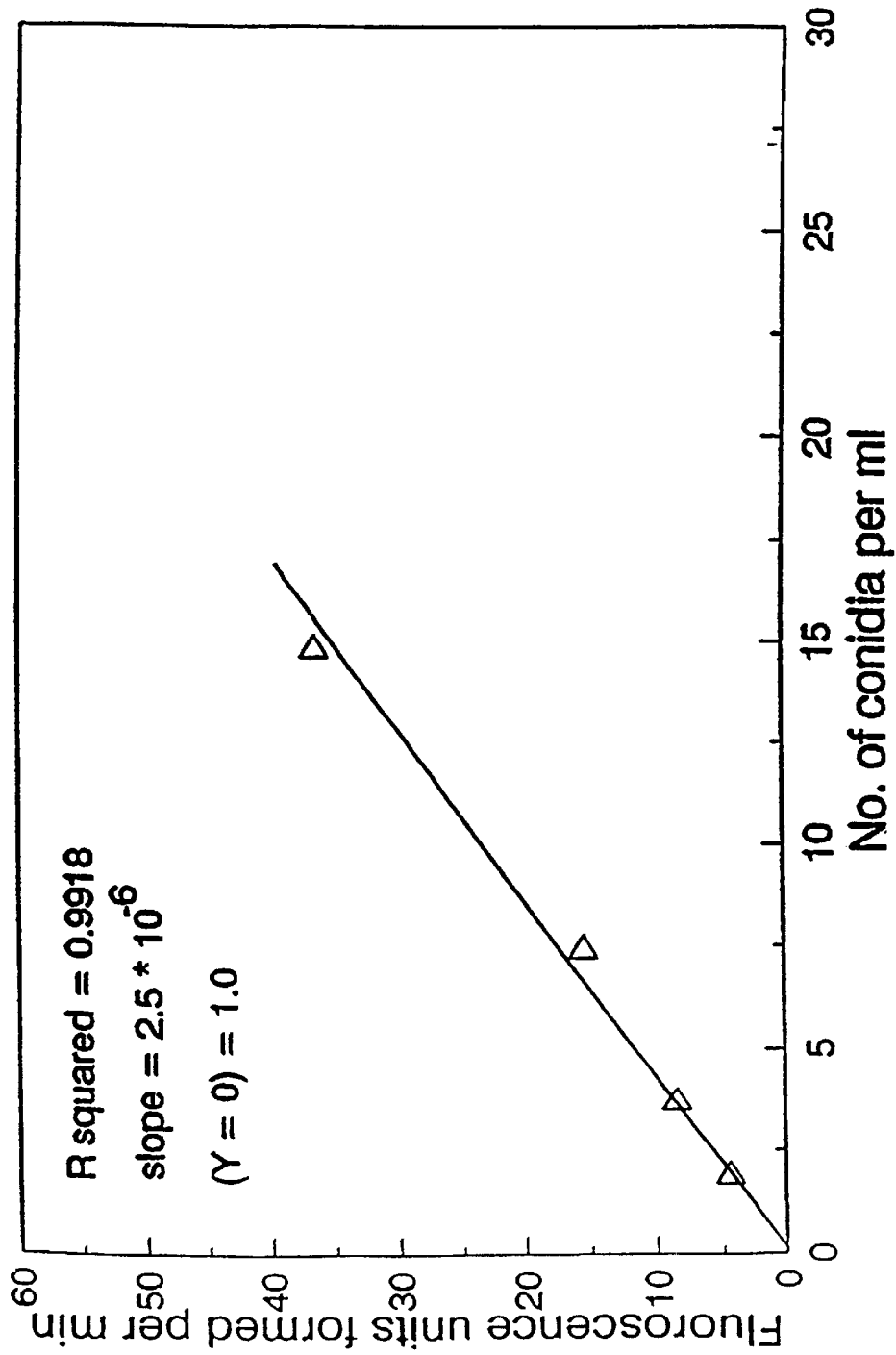
Figure 10:
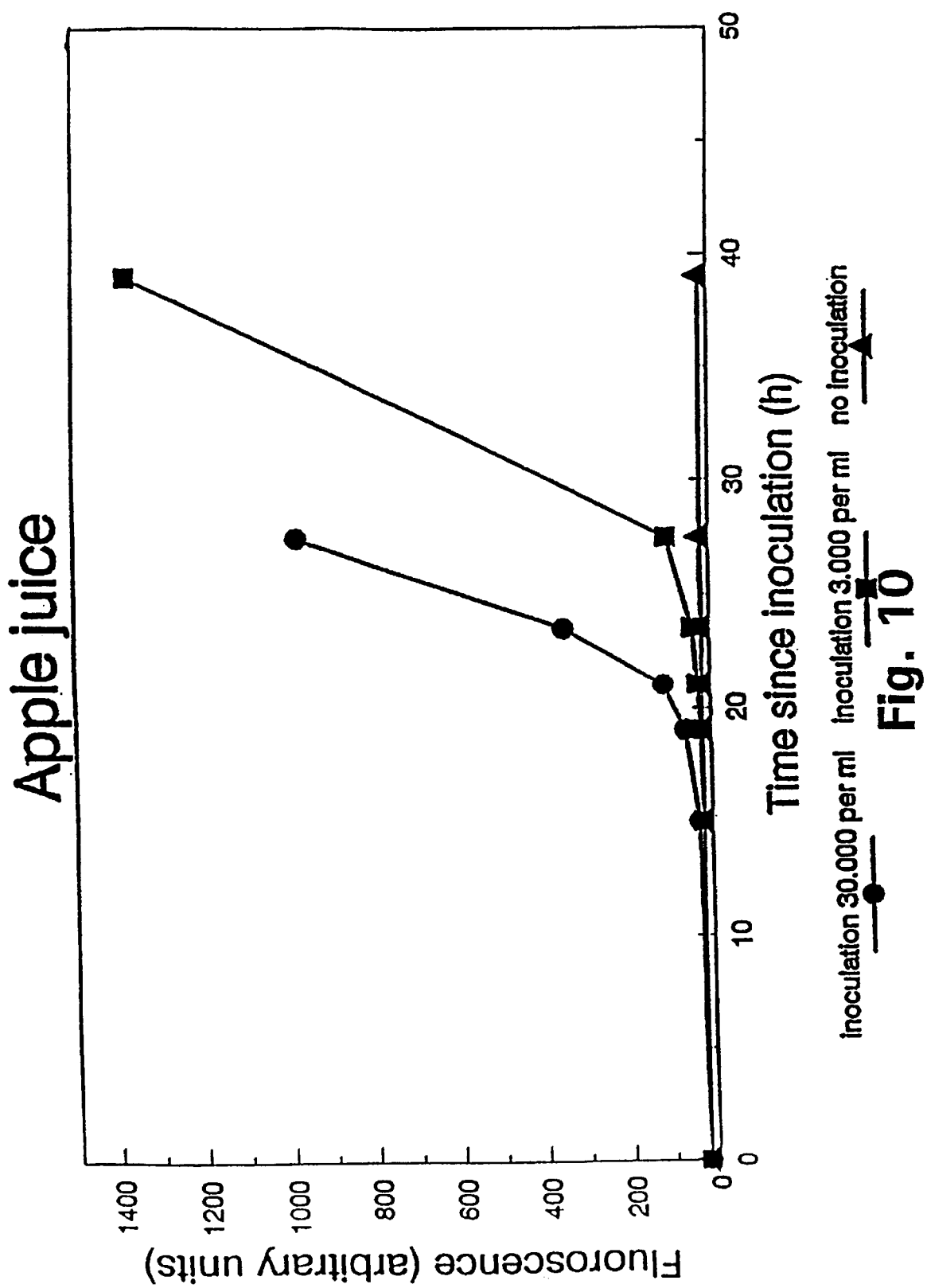
Figure 11:
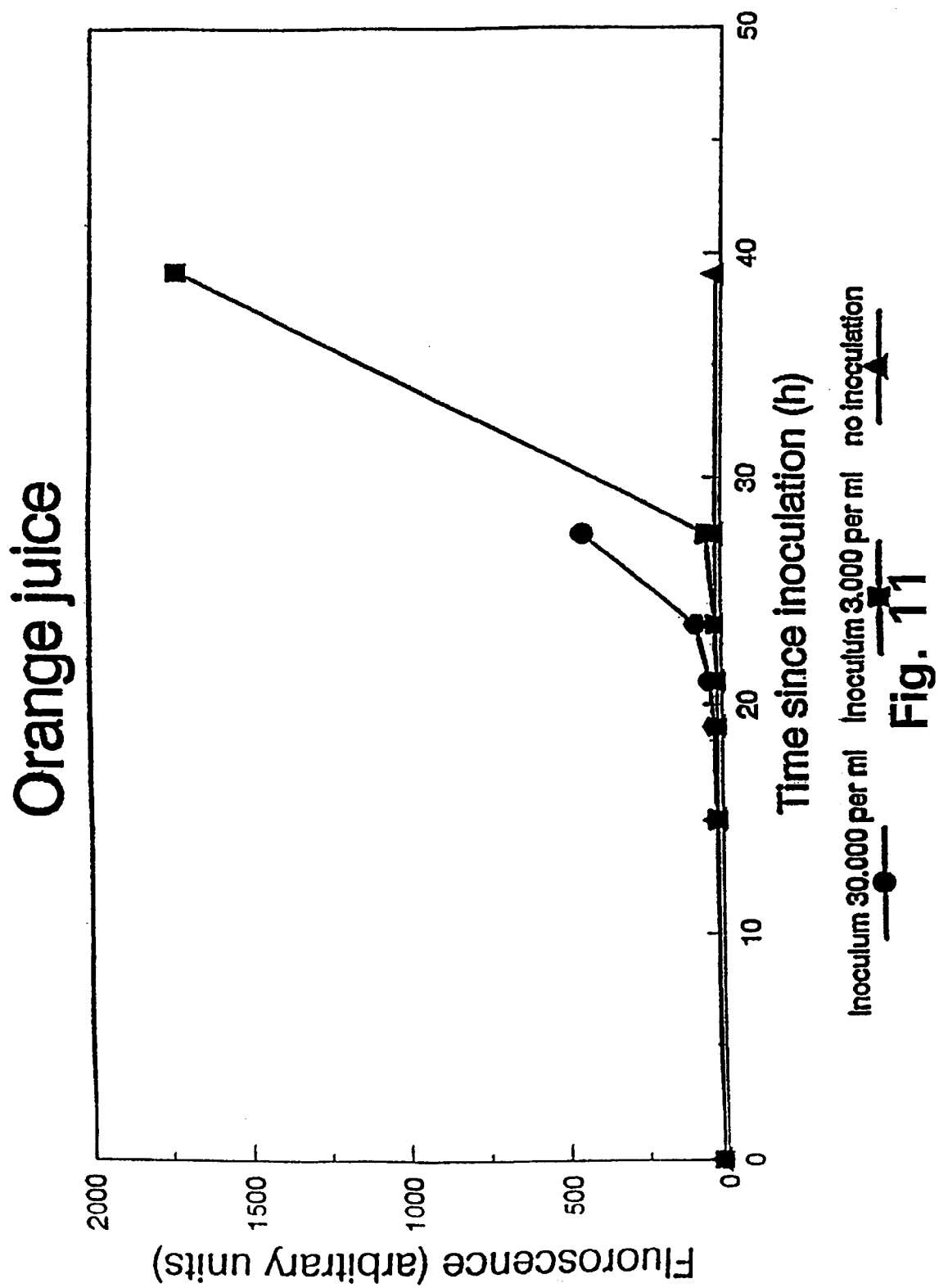
Figure 12:
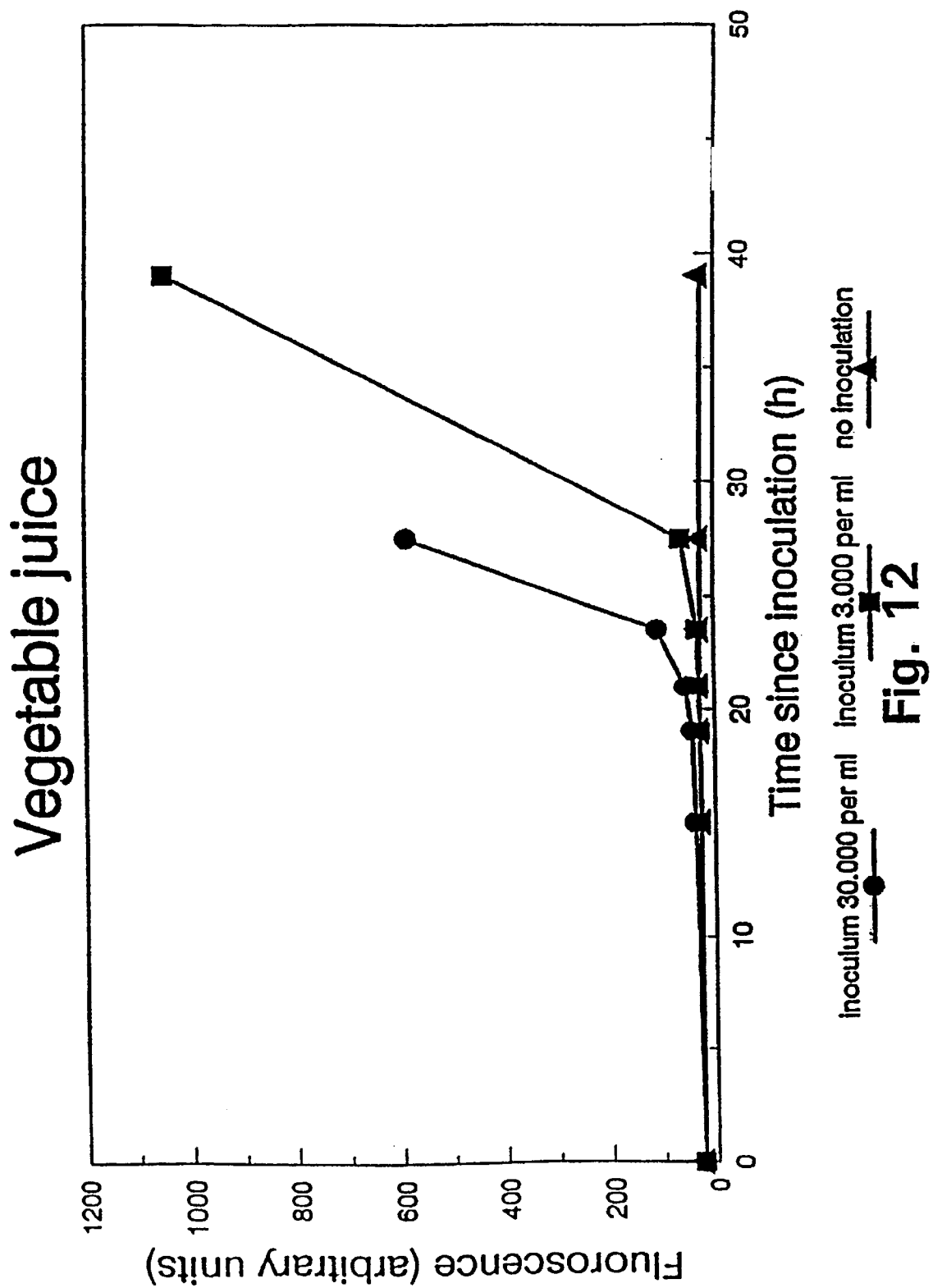

FIG. 7 shows the correlation between *Aureobasidium pullulans* biomass (mg dry weight) and fluorescence emitted by 4-methylumbelliferone (FU). All samples were contacted with 4-methylumbelliferyl-N-acetyl-β-D-glucosaminide (4-MU-GlcNAc) for 6 minutes. A. pullulans was grown in a chemostat culture at a dilution rate of 0.08 hours$^{-1}$. Samples were collected and the biomass diluted in order to assay minimum detectable amounts of fungal biomass, FIG. 8 illustrates the relationship between *Aureobasidium pullulans* biomass and fluorescence emitted by 4-methylumbelliferone (FU per mg dry weight per minute). Cultures of *A. pullulans* were grown in a chemostat at the dilution rates indicated in the figure. Samples were collected and contacted with 4-methylumbelliferyl-N-acetyl-β-D-glucosaminide (4-MU-GlcNAc) as described in Materials and Methods;

FIG. 9 shows quantitative detection of viable, non-growing fungal propagules in form of conidia (spores) of *Penicillium commune*. The result indicates correlation of dilutions of biomass comprising *P. commune* conidia (millions per ml) with fluorescence emitted by 4-methylumbelliferone (FU per minute). Samples were tested in accordance with the assay described in Materials and Methods;

FIG. 10 illustrates the time course of fluorescence emitted by 4-methylumbelliferone in pasteurized vegetable juice containing 4-methylumbelliferyl-Glcnac inoculated with blastoconidia of *Aureobasidium pullulans* at a concentration of 3.000 or 30.000 per ml;

FIG. 11 shows the time course of fluorescence emitted by 4-methylumbelliferone in pasteurized apple juice containing 4-methylumbelliferyl-Glcnac inoculated with blastoconidia of *Aureobasidium pullulans* at a concentration of 3.000 or 30.000 per ml; and FIG. 12 shows the time course of fluorescence emitted by 4-methylumbelliferone in pasteurized orange juice containing 4-methylumbelliferyl-Glcnac inoculated with blastoconidia of *Aureobasidium pullulans* at a concentration of 3.000 or 30.000 per ml.

EXAMPLES

Materials and Methods

Organisms Used

The fungi and bacteria used were obtained from the culture collection of the Institute of Biotechnology, Technical University of Denmark (IBT); the University of Massachusetts, Amherst, Mass. (QM); the Department of General Microbiology, University of Copenhagen, Denmark (AGM); and Department of Mycology and Phycology, University of Copenhagen, Denmark (AAS).

Media Used

The vegetable juice medium (V8) contained: 250 ml of Granini vegetable juice, $(NH_4)_2SO_4$, 0.5 g; $KH_2PO_4$, 0.5 g; Agar (Bacto agar, Difco Laboratories), 15.0 g. The volume was adjusted to 1 l with distilled water. Initial pH was adjusted with NaOH to 6.5.

The CYA-agar medium contained (g l$^{-1}$ distilled water): Sucrose, 30.0; yeast extract (Difco, Bacto-Yeast Extract), 5.0; $NaNO_3$.0; $K_2HPO_4$, 1.0; Kcl, 0.5; $MgSO_4.7H_2O$ and the following components (mg/l distilled water): $SO_4.7H_2O$, 10.0; $ZnCl_2$, 1.0; $CaCl_2.2H_2O$, 18.6; $MnCl_2.2H_2O$, 1.1; $CuCl_2.2H_2O$, 0.27; $NaMoO_4.2H_2O$, 0.22; $CoCl_2.6H_2O$, 0.28; $H_3BO_3$, 0.4; KI, 0.06. Agar (Bacto agar, Difco Laboratories) was added to a final concentration of 15 g l$^{-1}$.

The mineral medium which contained glucose as the only carbon source (15 g l$^{-1}$) was as described in Reeslev et al. (1993) except that agar was added to a concentration of 15 g l$^{-1}$. The SEA medium contained (g l$^{-1}$ distilled water): soil extract, 400 ml; glucose, 1; peptone, 1; yeast extract, 1; $K_2PO_4$, 1; agar, 15.

The chitin agar medium contained (g l$^{-1}$ distilled water): hydrolysed chitin precipitate, 10; $K_2HPO_4$, 1; $MgSO_4$ 7 $H_2O$, 0.5; NaCl, 0.5; $CaCl_2$, 0.1; $Fe(NH_4)_2(SO_4)_2.6H_2O$, 0.05; $NH_4Cl$, 0.1; agar, 15.

Hydrolysed chitin precipitate was prepared by adding: 10 g chitin (Fluka BioChemika) to 200 ml distilled water and kept overnight at 4° C. 400 ml 75% $H_2SO_4$ was added and the resulting solution left at 4° C. for 24 hours. The chitin was precipitated by mixing the solution with 9 l of 4° C. distilled water. After 48 hours the supernatant was decanted and the precipitate filtered to remove large pieces of undissolved chitin. The precipitate was centrifuged, washed with 0.2% $K_2HPO_4$ and the supernatant removed in 5–6 repeated cycles. The resulting hydrolysed chitin precipitate was then used in the preparation of the chitin agar. After autoclaving 2 ml (200 μM) of filter sterilized (0.2 μm) 4-methylumbelliferyl-β-D-glucosaminide were added to the agar media. Media were dispensed in 24 well microtiter plates and each well inoculated with a pure fungal or bacterial culture.

Detection of β-N-acetylglucosaminidase Activity in Selected Fungal and Bacterial Species A diverse selection of fungi and bacteria were screened on soil extract agar (SEA) and chitin agar containing 4-methylumbelliferyl-N-acetyl-β-D-glucosaminide. The microorganisms were cultivated in microtiter plates which were incubated at room temperature (21–23° C.) and were visually examined daily under UV light (366 nm) for eight days. Activity against 4-methylumbelliferyl-N-acetyl-β-D-glucosaminide was indicated by fluorescence. All screenings were in triplicate.

Screening of Selected Fungi for Several Enzyme Activities

A number of fungi representing different taxonomic groupings were screened for enzyme activity. The fungi were grown for in 24 well plates (Nunclon Multidish, Life Technologies A/S) (well volume 3.4 ml) containing 1.5 ml of agarized growth medium. After a growth period of 10 days at 25° C., 1.5 ml citrate-phosphat buffer (pH 5) were added to the wells and one of 11 enzyme substrates were then added to each well and incubated for 5 hours at 25° C. after which the fluorescence of each well was measured. For each fungus two wells were incubated with each enzyme substrate. All substrates were used in a final concentration of 10 μM. The substrate only and the organism plus the agarized medium were included as controls.

Microcosms Experiments 100 mg bulk soil was weighed into 10 ml plastic tubes. All assays were conducted at 25° C. in 2 ml 0.05 M tris-maleate buffer in four replicates. 4-methylumbelliferyl-N-acetyl-β-D-glucosaminide was added to a final concentration of 20 μM. Controls for extract, substrate fluorescence and quenching were processed in parallel. The assay was terminated by adding 2 ml ice cold 96% ethanol. After centrifugation, 2.7 ml supernatant was transferred to UV-plastic-cuvettes containing 300 μl 2.5 M tris buffer at pH 10. Fluorescence derived from the turnover of 4-methylumbelliferyl-N-acetyl-β-D-glucosaminide (liberated 4-methylumbelliferone, 4-MU) was determined with a luminescence spectrometer (Perkin-Elmer LS50, Buckinghamshire, UK) at 446 nm emission and 377 nm excitation.

Determination of Biomass Dry Weight and N-acetylglucosaminidase Activity

The fungi were grown on CYA-agar medium covered with cellophane membranes and growth was determined as colony radial growth rate, biomass dry weight and as the rate of degradation of 4-methylumbelliferyl-N-acetyl-β-D-glucosaminide. For all fungi the colony radial growth rate was constant during the time course of the experiments. The sampling was initiated when the colonies were from 2–35 mm in diameter depending on the species. The fungi were grown at 25° C. The cellophane membrane containing the fungal colony was gently lifted of the agar plate and placed in 3 ml citrate-phosphate buffer (pH 5). Substrate for β-N-acetylglucosaminidase (4-methylumbelliferyl-N-acetyl-β-D-glucosaminide) was added to a final concentration of 20 μM. It was ensured that the rate of degradation was constant during the incubation period. As the colonies grew the incubation time was gradually reduced (from 30 min to 2.5 min) in order to substantiate that less than 10% of the initial substrate was hydrolysed. The enzyme reaction was stopped by adding 3 ml 70% (v/v) ethanol.

Before monitoring the fluorescence the samples were centrifuged for 5 minutes at 4000 rpm. 1.7 ml supernatant was added to a cuvette containing 300 μl Tris buffer (2.5 M). The function of the TRIS-buffer (pH 10) was to increase the pH of the sample above pH 9 as fluorescence of 4-methylumbelliferone is pH dependent with a maximum emission above pH 8 (Fink & Koehler, 1972). The fluorescence (exitation 377 nm emission 446 nm) was monitored by use of a Perkin Elmer Luminescence spectrometer LS 50 B linked to an IBM compatible PC using software supplied by the manufacturer). The fluorescence at each biomass concentration was performed with triplicate determinations.

To obtain the biomass dry weight of the colony the pellet from the centrifugation was resuspended and filtered through a preweighed membrane filter (1.2 μm pore size) and dried to constant weight at 80° C.

Chemostat Experiment

Chemostat cultivations using the mineral medium were run at different dilution rates. The chemostat was run at a dilution rate 0.08 $h^{-1}$ and the pH and the temperature was kept constant at 5 and 27 degrees C. respectively (Reeslev et al., 1993) Samples taken from the chemostat were filtrated through a nylon mesh (pore size 41 μm) collecting the mycelium. The mycelium were then immediately resuspended in fresh medium containing 4-methylumbelliferyl-N-acetyl-β-D-glucosaminide.

Example 1

Detection of β-N-acetylhexosaminidase Activity and Other Enzyme Activities in Selected Fungal and Bacterial Species A diverse selection of fungi was screened on a mineral medium and a vegetable juice medium for their ability to degrade 11 4-methylumbelliferone-labelled substrates (Tables 1.1 and 1.2). The screening showed that the ability to degrade 4-methylumbelliferyl-GLcNAc (substrate 3 and 4 in Tables 1.1 and 1.2) could be demonstrated in all fungi tested. The same widespread degradation potential against other model substrates could not be demonstrated. The fungi subjected to the assaying procedure were all obtained from the culture collection of the Department of General Microbiology at the University of Copenhagen, Denmark.

TABLE 1.1

Enzyme activity of fungal species using eleven synthetic substrates in a mineral medium.
The enzymatic activity was determined as the amount of released 4-methylumbelliferone during hours of incubation (μmol): 0.4 ≦ * < 1; 1 ≦  2; 2 ≦ *.

|  | Enzyme substrates | | | | | | | | | | |
|---|---|---|---|---|---|---|---|---|---|---|---|
|  | 1 | 2 | 3 | 4 | 5 | 6 | 7 | 8 | 9 | 10 | 11 |
| *Aureobasidium pullulans* (QM 3092) | 0 | 0 | *** | *** | 0 | 0 | *** | 0 | 0 | * | 0 |
| *Paecilomyces farinosus* (AGM 5) | 0 | 0 | *** | ** | 0 | 0 | 0 | 0 | 0 | 0 | 0 |
| *Cladosporium herbarum* (AGM 8) | 0 | 0 | ** | * | 0 | 0 | 0 | 0 | 0 | 0 | 0 |
| *Penicillium commune* (IBT 13713) | 0 | 0 | ** | 0 | 0 | 0 | 0 | 0 | 0 | 0 | 0 |
| *Penicillium solitum* (IBT 13771) | 0 | 0 | *** | ** | 0 | 0 | 0 | 0 | 0 | 0 | 0 |
| *Aspergillus oryzae* (AGM 11) | 0 | 0 | *** | ** | 0 | 0 | 0 | 0 | 0 | 0 | 0 |
| *Mucor racemosus* (AAS 310) | * | 0 | *** | ** | 0 | 0 | 0 | 0 | 0 | 0 | 0 |
| *Ascobolus crenulatus* (AAS 1) | 0 | 0 | *** | ** | 0 | 0 | 0 | 0 | 0 | 0 | 0 |
| *Trametes versicolor* (AGM 24) | 0 | 0 | ** | ** | 0 | 0 | 0 | 0 | 0 | 0 | 0 |
| *Rhizomucor pusillus* (AAS 300) | 0 | 0 | * | *** | 0 | 0 | 0 | 0 | 0 | 0 | 0 |
| *Schizophyllum commune* (AGM 25) | * | 0 | *** | ** | 0 | 0 | 0 | 0 | 0 | 0 | 0 |
| *Sodaria fimicola* (AAS 17) | 0 | 0 | ** | ** | 0 | 0 | 0 | 0 | 0 | 0 | 0 |
| Eurotium sp. (AAS 36) | 0 | 0 | *** | ** | 0 | 0 | 0 | 0 | 0 | 0 | 0 |
| *Aspergillus versicolor* (IBT 13738) | 0 | 0 | ** | * | 0 | 0 | 0 | 0 | 0 | 0 | 0 |

1 = 4-methylumbelliferyl 7-6(sulfo-2-acetamido-2-deoxy-β-D-glucopyranoside);
2 = 4-methylumbelliferyl N-acetyl-α-D-glucosaminide;
3 = 4-methylumbelliferyl N-acetyl-β-D-blucosaminide;
4 = 4-methylumbelliferyl β-D-N,N',N"triacetylchitotrioside;
5 = 4-methylumbelliferyl α-D-mannopyranoside;
6 = 4-methylumbelliferyl β-D-mannopyranoside;
7 = 4-methylumbelliferyl α-D-glucoside;
8 = 4-methylumbelliferyl β-D-lactoside;
9 = 4-methylumbelliferyl β-D-xyloside;
10 = 4-methylumbelliferyl α-D-fucoside;
11 = 4-methylumbelliferyl β-D-fucoside.

TABLE 1.2

Enzyme activity of fungal species using eleven synthetic substrates in a vegetable juice medium.
The enzymatic activity was determined as the amount of released 4-methylumbelliferone during 5 hours of incubation ($\mu$mol): $0.4 \leq * < 1$; $1 \leq  \leq 2$; $2 \leq *$.

|  | Enzyme substrates | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| *Aureobasidium pulluians* (QM 3092) | 0 | 0 | *** | *** | ** | ** | *** | 0 | *** | 0 | 0 |
| *Paecilomyces farinosus* (AGM 5) | 0 | 0 | *** | 0 | 0 | 0 | 0 | 0 | 0 | 0 | 0 |
| *Cladosporium herbarum* (AGM 8) | 0 | 0 | ** | * | 0 | 0 | 0 | 0 | 0 | 0 | 0 |
| *Penicillium commune* (IBT 13713) | 0 | 0 | *** | *** | * | * | 0 | 0 | * | 0 | 0 |
| *Penicillium solitum* (IBT 13771) | 0 | 0 | *** | *** | 0 | 0 | 0 | 0 | ** | 0 | 0 |
| *Aspergillus oryzae* (AGM 11) | 0 | 0 | *** | *** | *** | *** | 0 | * | *** | 0 | 0 |
| *Mucor racemosus* (AAS 310) | * | 0 | *** | *** | * | ** | 0 | 0 | 0 | ** | 0 |
| *Ascobolus crenulatus* (AAS 1) | 0 | 0 | *** | ** | 0 | * | 0 | 0 | 0 | 0 | 0 |
| *Trametes versicolor* (AGM 24) | 0 | 0 | *** | *** | * | 0 | 0 | 0 | 0 | 0 | 0 |
| *Rhizomucor pusillus* (AAS 300) | 0 | 0 | *** | *** | *** | 0 | * | * | *** | *** | 0 |
| *Schizophyllum commune* (AGM 25) | 0 | 0 | *** | *** | ** | *** | 0 | ** | *** | 0 | 0 |
| *Sodaria fimicola* (AAS 17) | 0 | 0 | *** | *** | *** | *** | ** | ** | 0 | 0 | 0 |
| Eurotium sp. (AAS 36) | 0 | 0 | *** | ** | * | 0 | 0 | 0 | 0 | 0 | 0 |
| *Aspergillus versicolor* (IBT 13738) | 0 | 0 | *** | *** | 0 | 0 | 0 | 0 | *** | 0 | 0 |

Numbers indicates enzyme substrates as shown in Table 1.1.

In another experiment a diverse selection of fungi and bacteria were screened for their ability to degrade 4-methylumbelliferyl-GLcNAc when inoculated on soil extract agar (SEA) or a chitin-supplemented medium (chitin medium) (Tables 1.3 and 1.4). This experiment showed that except for 3 species all fungi were able to produce β-N-acetylhexosaminidase activity on SEA. Furthermore, two out of 3 fungal species previously showing no β-N-acetylhexosaminidase activity on SEA could be induced on the same medium supplemented with chitin. In contrast, only 7 bacterial species were able to produce β-N-acetylhexosaminidase activity and only on chitin-supplemented medium.

TABLE 1.3.

Fungal species producing β-N-acetylhexosaminidase activity on SEA and chitin agar

|  | β-N-acetylhexosamidase activity | |
| --- | --- | --- |
| Fungi | SEA[a] | Chitin agar |
| *Acremonium inflatum* (Mk001) | + | + |
| *Aspergillus flavus* (AGMf19) | + | + |
| Altetnaria sp. (AGMf4) | − | + |
| Beauveria sp. (AGMf35) | + | + |
| Botrytis sp. (AGMf10) | + | + |
| Candida albicans (AGMf11) | + | + |
| Cephalosporium sp. (AGMf13) | + | + |
| Cylindrocladium sp. (AGMf36) | + | + |
| Diplodia sp. (AGMf39) | + | + |
| *Fusarium solani (AGMf15)* | + | + |
| Geotrichum sp. (AGMf16) | + | + |
| Gliocladium sp. (AGMf17) | + | + |
| Humicola sp. (AGMf19) | + | + |
| *Lylea tetracoila* (Mk007) | + | + |
| Mucor sp. (AGMf20) | + | + |
| Penicillium sp. (AGMf22) | + | + |
| Paecilomyces sp. (AGMf21) | − | + |
| Rhodotorula sp. (AGMf26) | − | − |
| *Trichoderma polysporum* (ACMf31) | + | + |
| Trichurus sp. (AGMf30) | + | + |
| *Verticillium clamydosporium* (AGMf23) | + | + |

[a]SEA: Soil extract agar

TABLE 1.4.

Bacterial species producing β-N-acetylhexosaminidase activity on SEA and chitin agar

|  | β-N-acetylhexosamidase activity | |
| --- | --- | --- |
| Bacteria | SEA[a] | Chitin agar |
| *Alcaligenes faecalis* (AGMb4B) | − | − |
| *Arthrobacter simplex* (AGMb45) | − | − |
| *Bacillus cereus* (AGMb8) | − | − |
| *Bacillus megaterium* (AGMb134) | − | − |
| *Bacillus subtilis* (AGMb34) | − | − |
| *Bacillus thuringiensis* (AGMb18) | − | − |
| *Comamonas acidovarans* (AGMb56) | − | − |
| *Enterobacter aerogenes* (AGMb62) | − | − |
| *Eschericia coli* (AGMb30) | − | − |
| Klebsiella sp. (AGMb52) | − | + |
| *Micrococcus albus* (AGMb28) | − | − |
| *Micrococcus luteus* (AGMb5) | − | + |
| *Proteus vulgaris* (AGMb59) | − | + |
| *Pseudomonas aeruginosa* (AGMb23) | − | − |
| *Rhizobium meliloti* (AGMb60) | − | − |
| *Staphylococcus aureus* (AGMb20) | − | − |
| *Staphylococcus epidermis* (AGMb64) | − | − |
| *Staphylococcus faecalis* (AGMb21) | − | + |
| *Serratia marcescens* (AGMb3) | − | + |
| *Vibrio auguillarium* (AGMb46) | − | − |

[a] SEA: Soil extract agar

Example 2

Determination of Fungal Biomass in a Complex Environment

Figure 1:
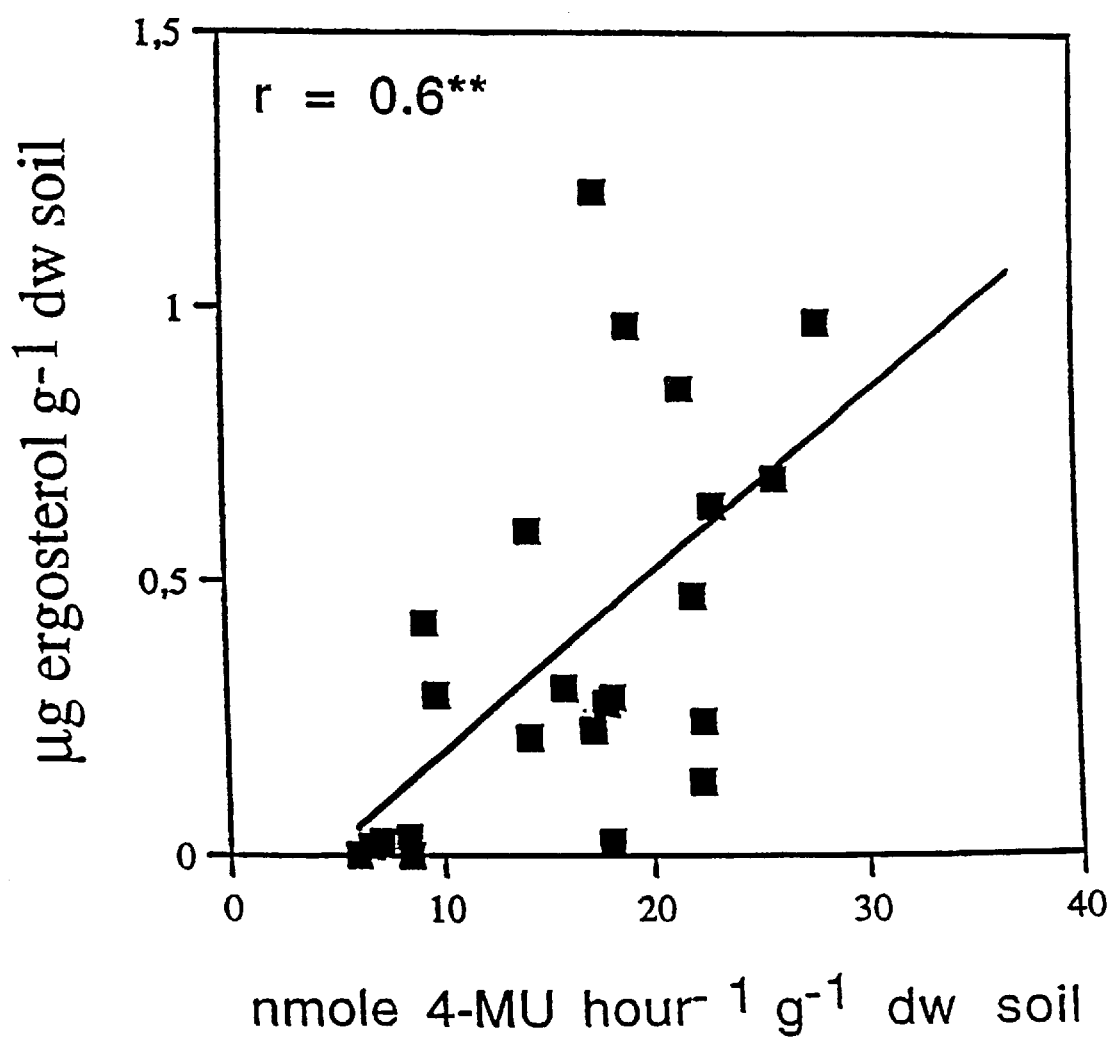
Figure 2:
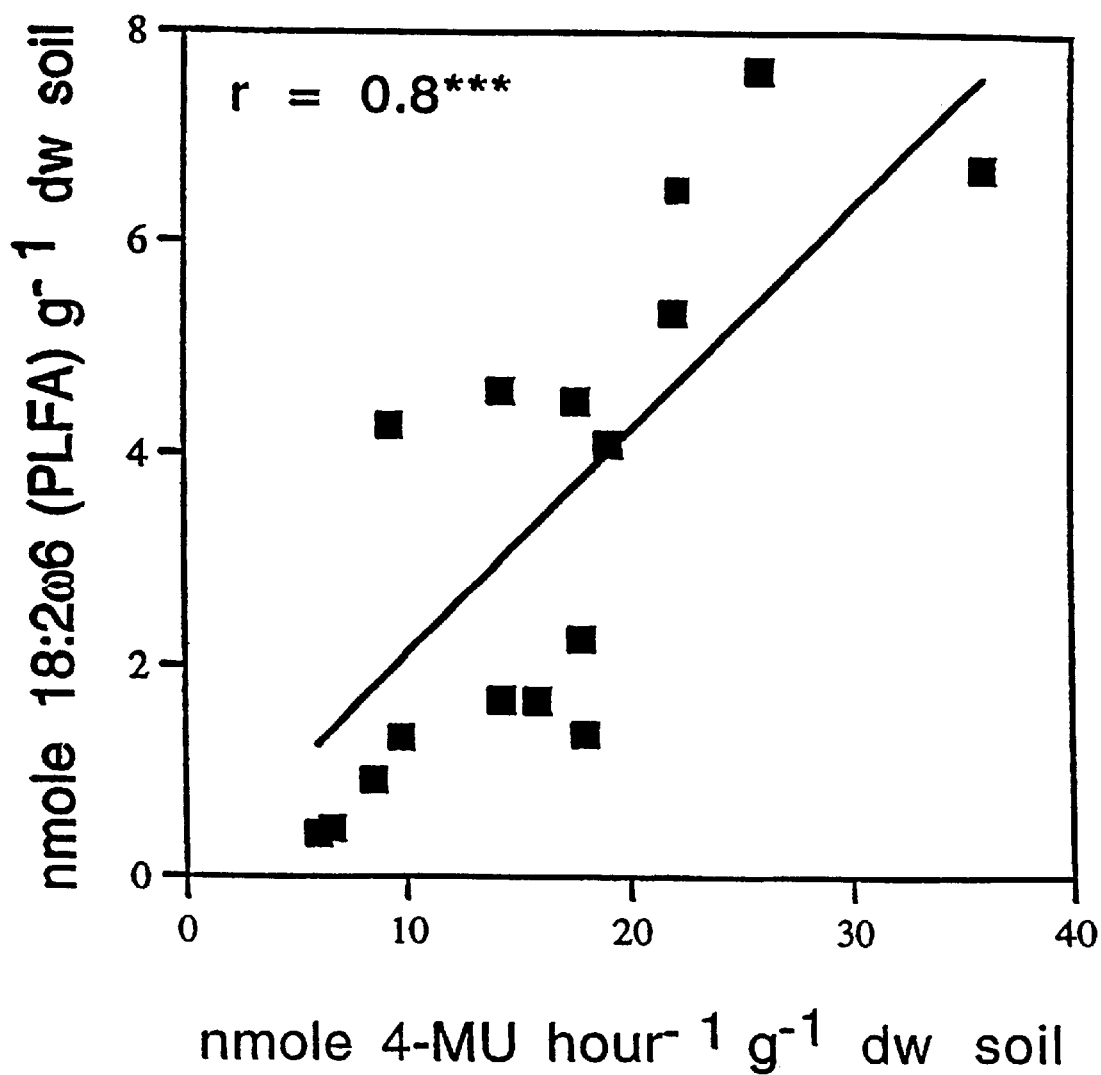

The present invention pertains in one aspect to a method of determining a fungal biomass present in a sample by detection of a fungal enzymatic activity present in the biomass. The detection of the fungal enzymatic activity involves contacting the sample with a substrate molecule comprising a detectable moiety released from said substrate in the presence of the fungal enzymatic activity. Demonstration of the highly significant, positive correlation between the detected fungal enzymatic activity-mediated 4-methylumbelliferone releasing cleavage of 4-methylumbelliferyl-N-acetyl-β-D-glucosaminide (4-MU- GlcNAc), as measured in nanomoles of cleaved 4-MU-GlcNAc per hour per cm$^3$ and estimates of the amount of the currently used state of the art fungal indicators ergosterol and PLFA, in selected soil samples, is presented in FIGS. 1 and 2, respectively.

The fact that this highly significant correlation was obtained in such a complex environment demonstrates the all-round application of the method provided in the present invention.

Figure 3:
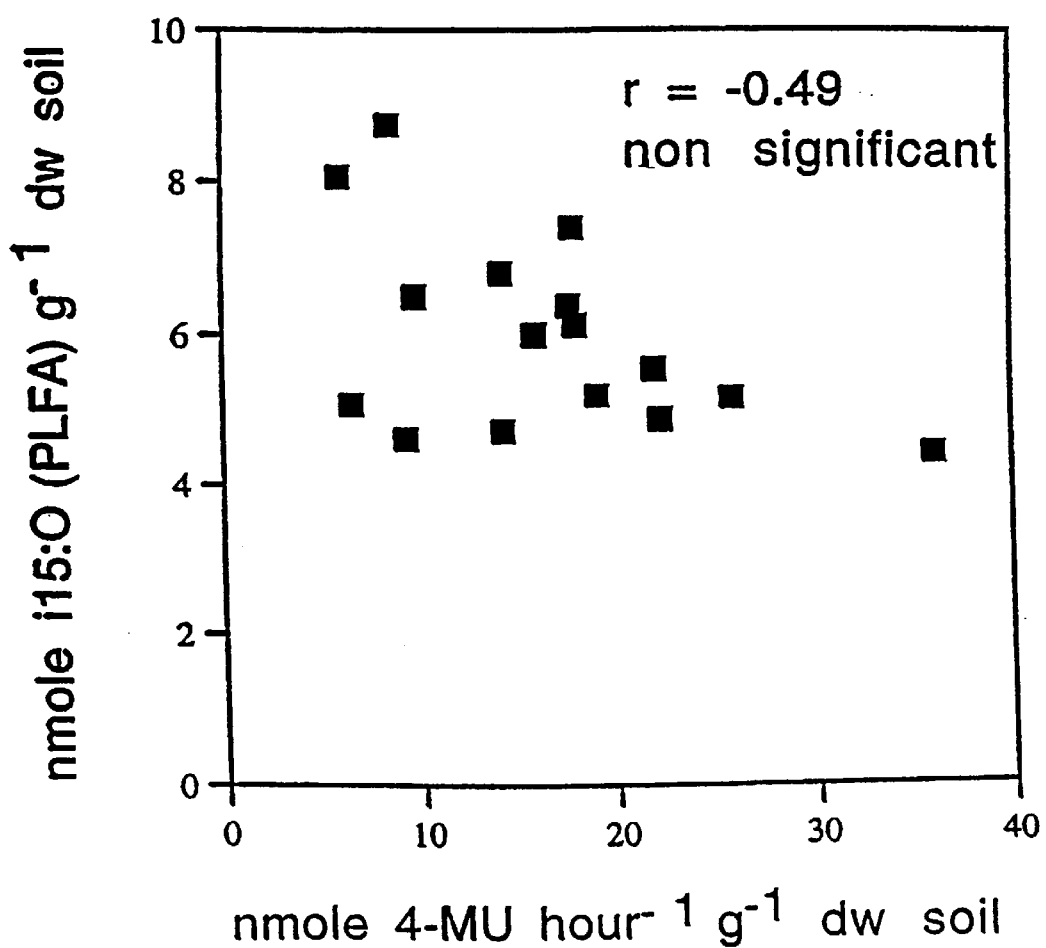
FIG. 3 shows the lack of a significant correlation between β-N-acetylhexosamidase activity as determined by the turnover of 4-methylumbelliferyl-N-acetyl-β-D-glucosaminide (4-MU-GlcNAc) and reported as the release of nmole 4-methylumbelliferone (4-MU) hour$^{-1}$ g$^{-1}$ dry weight (dw) soil, and the indicator of bacterial biomass, i15:0 PLFA (Frostegård and Bååth, 1996)

Furthermore, FIG. 3 shows the concurrent lack of a significant correlation between the content of a bacterial biomass index molecule i15:0 PLFA and β-N-acetylhexosaminidase activity in the soil samples, which confirms that β-N-acetylhexosaminidase activity is a specific indicator of fungal biomass in complex samples that also contain β-N-acetylhexosaminidase activity-producing non-fungal species.

Figure 4:
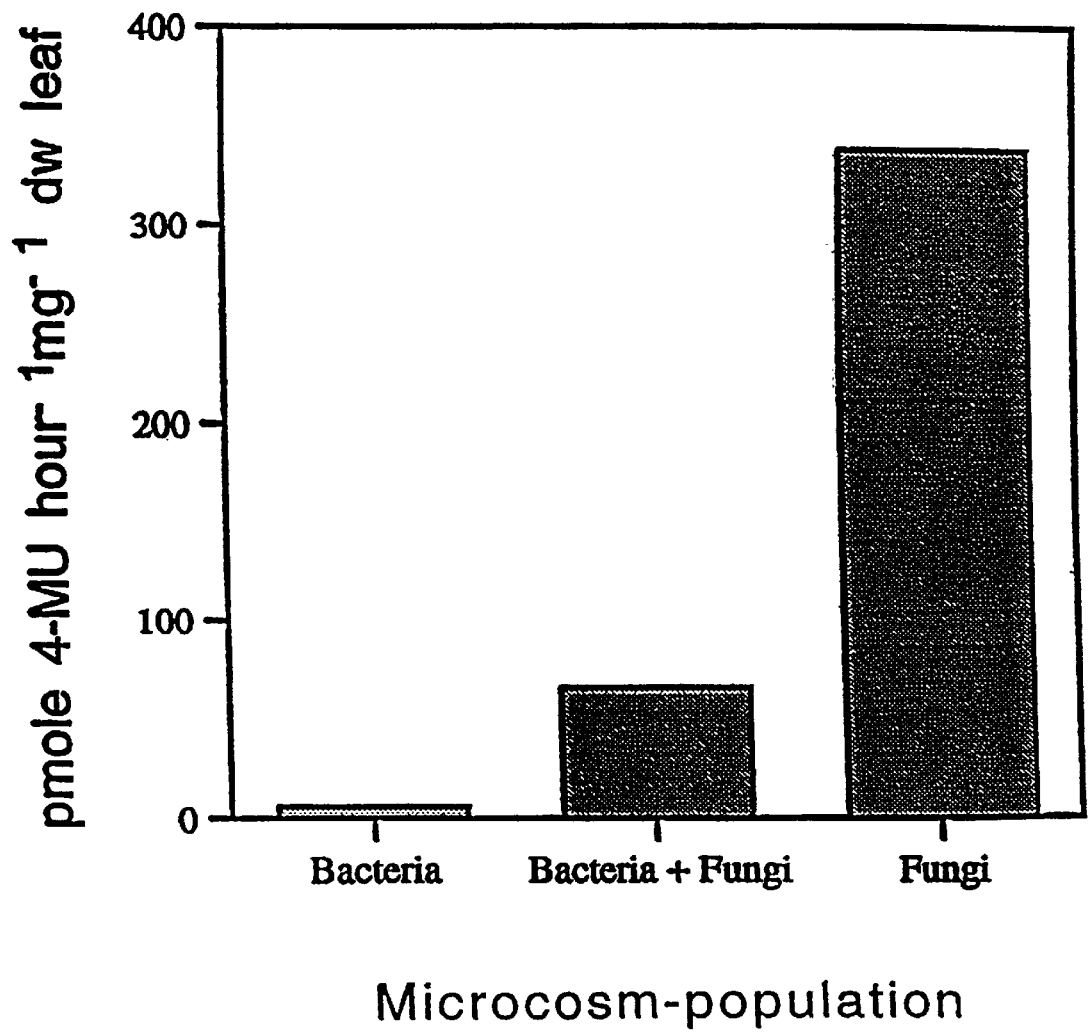
FIG. 4 shows the high correlation between presence and activity of fungi β-N-acetylhexosamidase activity as determined by the turnover of 4-methylumbelliferyl-N-acetyl-β-D-glucosaminide and reported as the release of 4-methylumbelliferone (4-MU) hour$^{-1}$ mg$^{-1}$ dry weight (dw) leaf.

A microcosm experiment was set up to evaluate β-N-acetylhexosaminidase activity as a specific indicator of the presence of fungi in a complex sample. Beech litter microcosm was inoculated with microbial populations isolated from a beech forest soil consisting of (i) bacteria from the beech forest soil isolated by centrifugation/homogenisation and devoid of fungal propagules, (ii) a suspension of bacteria and fungi representative of a natural microbial population in a beech forest soil and (iii) a monoculture of cellulolytic fungi (Hunicola sp.) isolated from beech leaves. Microcosm experiments showed that β-N-acetylhexosaminidase activities were 10 times higher in microcosms containing a mixture of bacteria and fungi and 60 times higher in microcosms containing fungi alone as compared to microcosms inoculated with a mixed bacterial population devoid of fungi (FIG. 4). The experiment demonstrated a high correlation between the presence and activity of fungi. Furthermore, the experiment showed that a mixed bacterial population with high functional diversity, as demonstrated by community level physiological profiles (BIOLOG), only contributed marginally to the β-N-acetylhexosaminidase activity.

Example 3

Correlation of β-N-acetylhexosaminidase with Fungal Biomass

Figure 5:
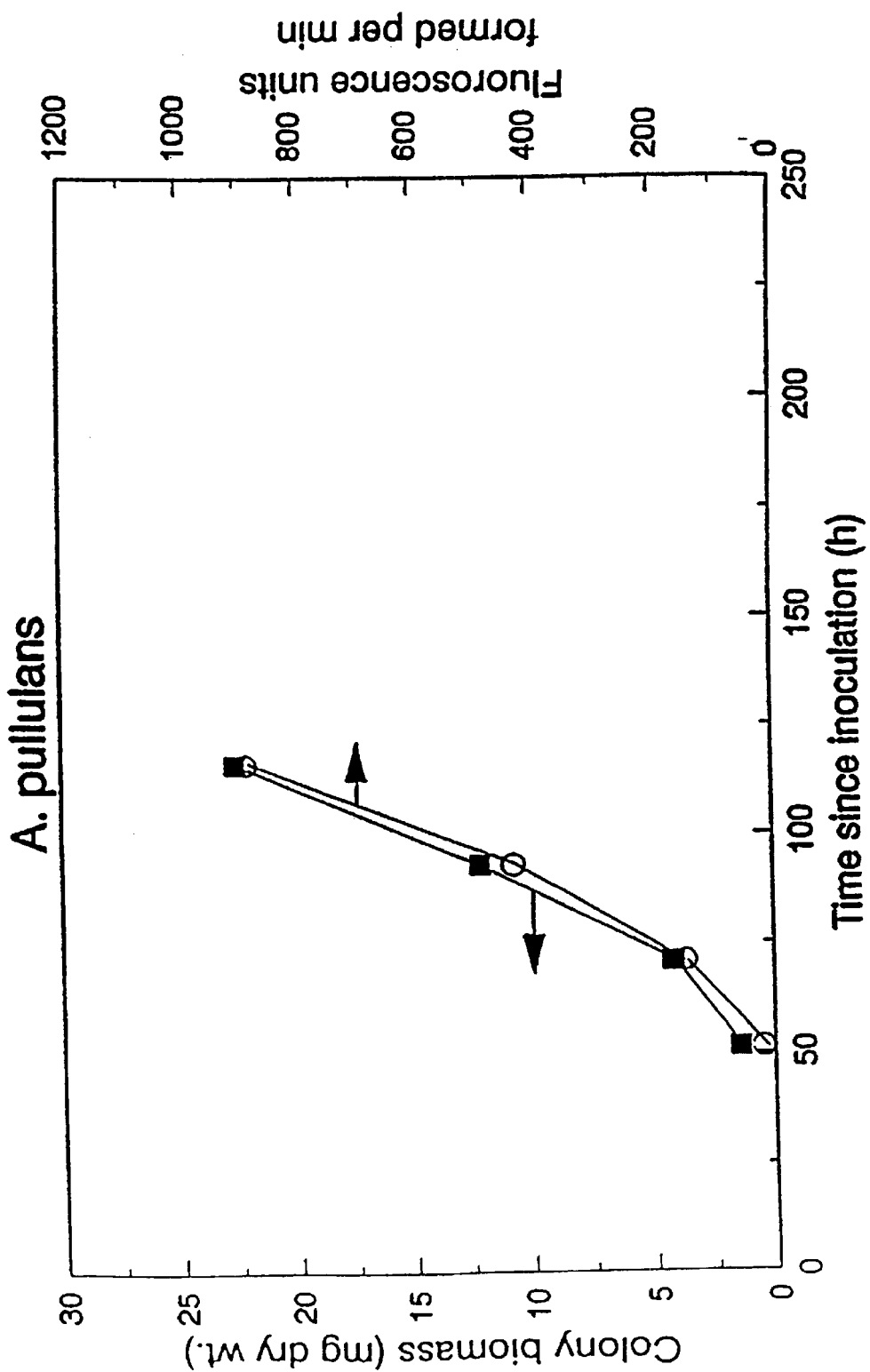
FIG. 5 illustrates the correlation between *Aureobasidium pullulans* biomass as measured in mg dry weight and the fluorescence emitted by 4-methylumbelliferone (FU per minute). Samples were collected at the indicated time-points and assayed in accordance with the assay described in Materials and Methods.
Figure 6:
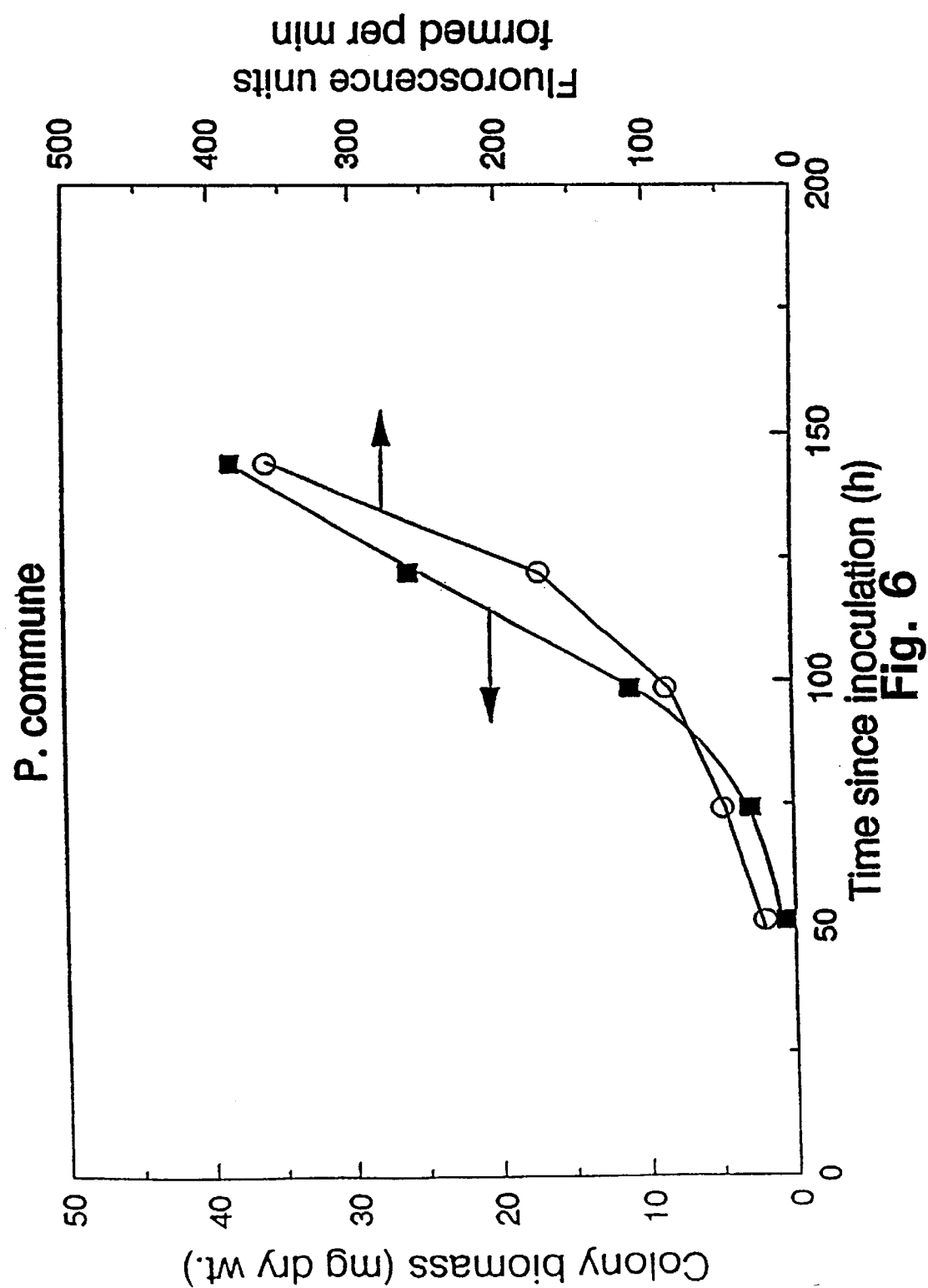
FIG. 6 illustrates the correlation between *Penicillium commune* biomass (mg dry weight) and fluorescence emitted by 4-methylumbelliferone (FU per minute). Samples were collected at the indicated time-points and assayed in accordance with the assay described in Materials and Methods.

Correlation between the detected substrate moiety and the amount of fungal biomass was demonstrated for cultures of *Aureobasidium pullulans* (FIG. 5) and *Penicillium commune* (FIG. 6) which were inoculated in a standard medium and grown under standard conditions. The biomass of each culture was measured in mg dry weight and correlated with the quantitatively detected 4-methylumbelliferone-mediated fluorescence measured (FU per minute). Samples for determination of biomass and detection of 4-methylumbelliferone were collected at the indicated timepoints and assayed as described in Materials and Methods. The results demonstrate a direct, positive correlation of fungal biomass with detected fluorescence.

Example 4

Determination of the Minimum Detectable Amount of Fungal Biomass

Having established a correlation between fungal biomass and the released substrate moiety, a determination of the minimum detectable amount of fungal biomass was performed.

*Aureobasidium pullulans* biomass was grown in a chemostat culture at a dilution rate of 0.08 hours$^{-1}$. A 20 ml sample was drawn from the chemostat and filtered through a nylon mesh (41 μm pore size) to retain the mycelium and remove single cells. The retained mycelium was washed with three volumes of incubation medium. A corresponding sample for determining the amount of fungal biomass was filtered through a membrane filter (1.2 μm pore size) and dried at 80° C.

The mycelium to be assayed was resuspended in 200 ml medium and samples and dilutions hereof were added to the assay medium calibrated to pH 5. At $T_0$, 0.2 ml 4-MU-GlcNAc was added to a final concentration of 40 μm in a total volume of 2 ml. The contacting of the sample and 4-MU-GlcNAc was performed for 6 minutes at 25° C. At T=6 min., around 12 minutes after having redrawn the sample from the chemostat, the reaction was stopped by addition of 2 ml ice cold 96% (v/v) ethanol.

Correlation of the quantitatively detected fluorescence with the assayed fungal biomass, measured as dry weight, is shown in FIG. 7. The results demonstrate that fungal biomass in an amount of less than 2 mg dry weight per liter is detected with an incubation time of 6 minutes. The actual amount of fungal biomass present in the sample was less than 4 μg. By increasing the time of contacting the sample with the substrate molecule it is possible to detect an amount of fungal biomass of less than 0.1 μg.

Example 5

Correlation Between β-N-acetylhexosaminidase Activity and the Growth Rate of Fungal Biomass As illustrated in FIG. 8, a correlation between *Aureobasidium pullulans* biomass (mg dry weight) and the quantitatively detected fluorescence emitted by 4-methylumbelliferone (FU per mg dry weight per minute) can be established for a set of different chemostat dilution rates while keeping all other parameters constant.

The cultures were carbon-limited (in order to obtain the highest possible proportion of mycelial cells over yeast) (Reeslev et al. 1993). Furthermore, precautions were taken to avoid any decline of the steady state biomass often seen at higher dilution rates and which can indicate a shift in the limiting nutrient and thereby the cell metabolism.

Cultures of *A. pullulans* were grown in SYN-medium in a chemostat at the dilution rates indicated in FIG. 8. Samples were drawn from the chemostat and filtered through a nylon mesh (pore size 41 μm) to remove single cells and retain the mycelium. Samples were resuspended as described above and contacted with 4-methylumbelliferyl-N-acetyl-β-D-glucosaminide (4-MU-GlcNAc) as described in Materials and Methods.

Example 6

Determination of Fungal Biomass Comprising Conidia

Quantitative detection of non-growing propagules such as conidia (spores) of *Penicillium commune* was also achieved by using the assay procedure described in Materials and Methods. The results shown in FIG. 9 demonstrate a direct correlation between dilutions of biomass comprising *P. commune* conidia (millions per ml and the quantitatively detected fluorescence emitted by 4-methylumbelliferone (FU per minute). Samples were tested in accordance with the assay described in Materials and Methods.

Example 7

Detection of Fungal Biomass in Food Products

Pasteurized apple juice, orange juice and vegetable juice were inoculated with blastoconidia of *A. pullulans* at a final concentration of 3,000 and 30,000 per ml and 4-methylumbelliferyl-N-acetyl-β-D-glucosaminide as the substrate was added to a final concentration of 110 μM. Samples were withdrawn under sterile conditions and the fluorescence determined. FIGS. 10, 11 and 12 show that the detection times as determined by the degradation of the substrate were between 22 and 25 hours at 30,000 conidia per ml and about 29 to 32 hours at 3,000 conidia per ml.

Inhibition of germination of blastoconidia of *A. pullulans* due to crowding effect does not occur at concentrations of less than about $1 \times 10^6$ per ml and therefore, the time required for germination should not be affected when lower inoculum concentrations are used. Also, the difference in inoculum density should not affect the specific growth rate in the experiments. Consequently, the difference in detection time of about 7 hours relates to the difference in the initial concentration of blastoconidia. Based on these assumptions, the detection time for juice containing 1 conidium per ml can by extrapolation be estimated to be about 53 hours.

Example 8

Detection of Fungal Biomass Associated with Building Materials

Samples from the ceiling boards of a school building with fungal (mould) problems were taken prior to and after cleaning. By visual examination three areas were chosen for the experiment: one area with no visible fungal growth, an area appearing slightly contaminated and an area with apparent fungal growth.

Area 1: strong black discolouration of the ceiling boards

Area 2: the ceiling boards slightly grubby

Area 3: no visible discolouration

Three samples were taken from each area. The samples were taken by gently rubbing area of 5 cm$^2$ of the ceiling with sterile swabs. The swabs were incubated for 1 hour or less in a buffer containing a substrate 4-methylumbelliferyl-N-acetyl-β-D-glucosaminide after which the swab was removed followed by addition of 2.5 M Tris and the fluorescence was determined. The results (Table 8.1) showed good correspondence with visual observations and to an agar plate imprint. The agar plate imprints were evaluated during a period of 7 days.

TABLE 8.1.

Fluorescence units formed (–control) by samples taken from ceiling boards before and after cleaning. Samples were incubated for 1 hour

|  | prior to cleaning (fluoroscence units) | | | after cleaning (fluoroscence units) | | |
|---|---|---|---|---|---|---|
| Area 1 | 3010 | 3527 | 3120 | 0 | 0 | 0 |
| Area 2 | 1536 | 1733 | 2537 | 5 | 0 | 0 |
| Area 3 | 0 | 0 | 0 | 0 | 0 | 0 |

The agar imprint method gave the following results:

prior to cleaning

Area 1: >50 colonies

Area 2: <10 colonies

Area 3: no growth after cleaning

Area 1: no growth

Area 2: no growth

Area 3: no growth

Example 9

Determination of Fungal Biomass in a Sample of Wood

The method of detecting a fungal biomass was used for "in situ" assaying a sample of wood known to be contaminated with propagules of *Serpula lacrymans*. A sample was assayed as described in Materials and Methods and after a contacting time of 20 minutes a fluorescence corresponding to 840 fluorescence units (FU) was measured.

In a control experiment, a similar block of wood also known to comprise *S. lacrymans* was autoclaved prior to assaying and no fluorescence was detectable when the sample was subjected to assaying (a value of 0 FU was obtained).

The method can thus be used to evaluate the effect of a given fungicide treatment of wood or the effect of any treatment directed towards eliminating the growth of a fungal biomass in wood. In particular, the method can be used for detection of fungal infections of trees and plants, e.g. infections by *Ophiostoma novo ulmi* causing Dutch Elm disease.

Example 10

Diagnostic Method for the Detecting Fungal Infections In Humans

The diagnostic method detects fungal β-N-acetylhexosaminidase activity in human plasma. It was found that 4-methylumbelliferyl-N-acetyl-β-D-glucosaminide is also cleaved by human hexosaminidase normally present in blood and plasma samples. However, it was discovered that this human hexosaminidase activity can be eliminated by a pre-treatment step comprising precipitation e.g. by adding ammonium sulphate (70% saturation) to the human plasma samples. This was demonstrated in plasma samples containing *Candida albicans* or *Aspergillus fumigatus* culture fluids in which *C. albicans* or *A. fumigatus* β-N-acetylhexosaminidase activity was present. In the samples containing *C. albicans* culture fluid more than 75% of the fungal β-N-acetylhexosaminidase activity remained after precipitation step to eliminate interfering human enzyme activity.

The assay mixture typically comprises 100 μl of the pre-treated plasma supplemented with culture fluid, 100 μl phosphate/citrate buffer, pH 5, and 50 μl (1.2 mM) substrate (4-methylumbelliferyl-N-acetyl-β-D-glucosaminide). After incubation, 300 μl Tris buffer (2.5 M) was added to the mixture to increase the pH to above 9 and the fluorescence measured. This procedure was tested on plasma from different control subjects with no known previous fungal infections. Culture fluids from cultivation of *C. albicans* or of *A. fumigatus* containing β-N-acetylhexosaminidase activity were added to the plasma samples. Following a pre-treatment as described above, 4-methylumbelliferyl-N-acetyl-β-D-glucosaminide and buffer was added and the plasma was incubated. After the incubation, Tris buffer was added and the fluorescence formed was measured against the control samples. The presence of fungal β-N-acetylhexosaminidase activity was detected and the fluorescence was proportional to the amount of fungal β-N-acetylhexosaminidase added.

REFERENCES

Claeyssens M., Van Tilbeurgh H., Tomme P and T. M. Wood (1989). Fungal cellulase systems: Comparison of the specificities of the cellobiohydrolases isolated from *Penicillium pinophilum* and *Trichoderma reesi*. Biochemical Journal 261, 819–625.

Fink D. W. and W. R. Koehler (1972). pH effects on fluorescence of umbelliferone. Analytical Chemistry 42, 990–993.

Frostegård Å., Tunlid A. and E. Bååth (1993). Phospholipid fatty acid composition, biomass and activity of microbial communities from two soil types experimentally exposed to different heavy metals. Applied and Environmental Microbiology 11, 3605–3617.

Frostegård, A. and Bååth, E. (1996) The Use of Phospholipid Fatty Acid Analysis to Estimate Bacterial and Fungal Biomass in Soil; Biol. Fertil. Soils 22,59–65.

Grant W. D. and A. W. West (1986). Measurement of ergosterol, diaminopimelic acid and glucosamine in soil: Evaluation as indicators of microbial biomass. Journal of Microbiological Methods 6, 47–53.

Kropp B. R. (1990). Variable interactions between non-mycorrhizal and ectomycorrhizal strains of the basidiomycetes Lacaria bicolor. Mycological Research 94, 412–415.

McCreath K. J. and G. W. Gooday (1992). A rapid and sensitive microassay for determination of chitinolytic activity. Journal of Microbiological Methods 14, 229–237.

Reeslev M., Jørgensen B. B. and Jørgensen O. B. (1993). Influence of $Zn^{2+}$ on yeast-mycelium dimorphism and exopolysaccharide production by the fungus *Aureobasidium pullulans* grown in a defined medium in continuous culture. Journal of General Microbiologi 139, 3065–3070.

What is claimed is:

1. A method of selectively detecting a fungal biomass in a sample, comprising the steps of
   (i) detecting the amount, presence or activity of β-N-acetylhexosaminidase in said sample, and
   (ii) correlating the amount, presence or activity of β-N-acetylhexosaminidase with at least one fungal biomass parameter, the detection being made under conditions where β-N-acetylhexosaminidase of non-fungal origin, if present, cannot be detected.

2. A method according to claim 1 wherein the amount, presence or activity of β-N-acetylhexosaminidase is detected by
   (i) contacting the sample with a substrate molecule comprising a detectable moiety releasable from said substrate molecule in the presence of β-N-acetylhexosaminidase, and
   (ii) detecting the release moiety.

3. A method according to claim 1 wherein the amount, present or activity of β-N-acetylhexosaminidase is detected immunologically.

4. A method according to claim 1 wherein the fungal biomass parameter comprises at least one of: the amount of fungal biomass present in the sample as determined directly by measuring the weight of the fungal biomass, a metabolite, an additional enzymatic activity and an indicator of the physiological state of said fungal biomass.

5. A method according to claim 1 wherein the fungal biomass comprises at least one of the following fungi: Zygomycotina, Ascomycotina, Basidiomycotina or Deuteromycotina.

6. A method of claim 2 wherein the substrate molecule comprises a fluorogenic moiety, a chromogenic moiety, or a mixture thereof.

7. A method according to claim 2 wherein the released moiety is 4-methylumbelliferone or a fluorescently detectable derivative thereof.

8. A method according to claim 7 wherein the substrate molecule is 4methylumbelliferyl-N-acetyl-β-D-glucosaminide.

9. A method according to claim 2 which permits an amount of less than 1 picomole of the released moiety to be detected.

10. A method according to claim 2 wherein the released moiety is detected over time at pre-determined intervals or continuously.

11. A method according to claim 10 wherein the released moiety is detected by on-line analysis.

12. A method according to claim 2 comprising the detection of at lease one additional substrate molecule comprising a detectable moiety.

13. A method according to claim 2 wherein the time on contacting the sample with the substrate molecule is about 30 minutes or less.

14. A method according to claim 1 permitting the detection of an amount of fungal biomass ranging from at least about 0.001 µg to at least about 1 µg.

15. A method according to claim 1 wherein the sample comprises an environmental sample, a food product, a plant material, a building material or an industrial fungal culture.

16. A method according to claim 1 wherein the sample is collected from a human being or an animal.

17. A method according to claim 15 or 16 wherein the sample is pre-treated in order to reduce or eliminate a non-fungal β-N-acetylhexosaminidase activity inherently present in such a sample.

18. A method according to claim 1 wherein the conditions under which β-N-acetylhexosaminidase of non-fungal origin, if present, cannot be detected include the use of agents that selectively inhibit growth of non-fungal microbial species or enzymatic activity of such species.

19. A method according to claim 1 wherein the conditions under which β-N-acetylhexosaminidase of non-fungal origin, if present, cannot be detected include the use of cultivation methods where non-fungal enzymatic activity cannot be expressed.

20. A method according to claim 1 wherein the at least one fungal biomass parameter relates to the amount of ergosterol present in the sample.

21. A method according to claim 1 permitting the detection of an amount of fungal biomass of at least about 0.001 µg.

22. A method according to claim 1 permitting the detection of an amount of fungal biomass of at least about 0.01 µg.

23. A method according to claim 1 permitting the detection of an amount of fungal biomass of at least about 0.1 µg.

24. A method according to claim 4 wherein the fungal biomass parameter comprises ergosterol or phospholipid fatty acids (PLFA).

25. A method according to claim 2 wherein the substrate molecule is 4-methylumbelliferyl-β-D-N,N',N"-triacetylehitotrioside.

26. A method according to claim 2 wherein the substrate molecule comprises a 4-methylumbelliferone moiety.

27. A method according to claim 2 wherein the substrate molecule comprises a derivative of 4-methylumbelliferone moiety.

* * * * *